(12) United States Patent
Engles et al.

(10) Patent No.: US 8,268,336 B2
(45) Date of Patent: *Sep. 18, 2012

(54) COMPOSITIONS CONTAINING AROMATIC ALDEHYDES AND THEIR USE IN TREATMENTS

(75) Inventors: Charles R. Engles, Portola Valley, CA (US); Bryan Fuller, Edmond, OK (US); Brian Keith Pilcher, Edmond, OK (US)

(73) Assignee: Skinmedica, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/407,029

(22) Filed: Feb. 28, 2012

(65) Prior Publication Data

US 2012/0157546 A1    Jun. 21, 2012

Related U.S. Application Data

(63) Continuation of application No. 10/223,073, filed on Aug. 15, 2002.

(60) Provisional application No. 60/332,277, filed on Nov. 16, 2001, provisional application No. 60/346,049, filed on Jan. 4, 2002, provisional application No. 60/368,518, filed on Apr. 1, 2002, provisional application No. 60/384,589, filed on May 30, 2002.

(51) Int. Cl.
 *A61K 8/02* (2006.01)
 *A61K 31/11* (2006.01)

(52) U.S. Cl. ........................................ 424/401; 514/699
(58) Field of Classification Search .................. 424/401; 514/699
See application file for complete search history.

(56) References Cited

U.S. PATENT DOCUMENTS

| | | | |
|---|---|---|---|
| 3,845,138 A | 10/1974 | Dunlop et al. | |
| 4,126,695 A | 11/1978 | Razdan et al. | |
| 4,147,770 A | 4/1979 | Sichak | |
| 4,202,877 A | 5/1980 | Sato et al. | |
| 4,290,974 A | 9/1981 | Boillon et al. | |
| 4,391,603 A | 7/1983 | Rosenbaum et al. | |
| 4,654,167 A | 3/1987 | Degner et al. | |
| 4,668,712 A | 5/1987 | Hino et al. | |
| 4,714,609 A | 12/1987 | Carden et al. | |
| 4,714,786 A | 12/1987 | Wuest et al. | |
| 4,997,850 A | 3/1991 | Kimura et al. | |
| 5,100,654 A | 3/1992 | Pawelek et al. | |
| 5,217,709 A | 6/1993 | Lagrange et al. | |
| 5,508,310 A | 4/1996 | Rhodes | |
| 5,614,179 A | 3/1997 | Murphy et al. | |
| 5,626,852 A | 5/1997 | Suffis | |
| 5,656,638 A | 8/1997 | Gaeta et al. | |
| 5,668,182 A | 9/1997 | Abraham et al. | |
| 5,733,535 A | 3/1998 | Hollingshead et al. | |
| 5,747,537 A | 5/1998 | Gordon et al. | |
| 5,760,085 A | 6/1998 | Beck et al. | |
| 5,766,575 A | 6/1998 | Crotty et al. | |
| 5,968,484 A | 10/1999 | Habeck et al. | |
| 6,086,903 A | 7/2000 | Trinh et al. | |
| 6,126,930 A * | 10/2000 | Dubois et al. ................ | 424/73 |
| 6,146,650 A | 11/2000 | Redlinger | |
| 6,204,229 B1 | 3/2001 | Hasegawa | |
| 6,214,879 B1 | 4/2001 | Abraham | |
| 6,248,763 B1 | 6/2001 | Scivoletto | |
| 6,264,927 B1 | 7/2001 | Monahan | |
| 6,403,063 B1 | 6/2002 | Sawyer | |
| 6,475,526 B1 | 11/2002 | Smith | |
| 6,673,844 B2 | 1/2004 | Kumamoto et al. | |
| 2003/0124157 A1 | 7/2003 | Engles et al. | |
| 2003/0157154 A1 | 8/2003 | Fuller et al. | |
| 2004/0254252 A1 | 12/2004 | Engles et al. | |
| 2008/0004354 A1 | 1/2008 | Engles et al. | |

FOREIGN PATENT DOCUMENTS

| | | |
|---|---|---|
| DE | 3 214 658 | 11/1982 |
| EP | 0022229 A1 | 1/1981 |
| EP | 0 044 970 | 2/1982 |
| EP | 0 044 976 | 2/1982 |
| EP | 0193257 | 9/1986 |
| EP | 0 332 175 | 9/1989 |
| EP | 0395441 | 10/1990 |
| EP | 0635208 | 1/1995 |
| EP | 0914817 A1 | 5/1999 |
| EP | 0985408 | 3/2000 |
| GB | 1545954 | 5/1979 |
| GB | 2244645 | 12/1991 |
| JP | 52044375 | 11/1977 |
| JP | 55045656 | 3/1980 |
| JP | 55045659 | 3/1980 |
| JP | 56012310 | 2/1981 |
| JP | 60067424 A | 4/1985 |
| JP | 61257904 | 11/1986 |
| JP | 6048929 | 2/1994 |
| JP | 6329516 | 11/1994 |

(Continued)

OTHER PUBLICATIONS

Arnold et al. "Evaluation of chemopreventive agents in different mechanistic classes using a rat tracheal epithelial cell culture transformation assay" Cancer Res. 55:537 (1995).

(Continued)

*Primary Examiner* — Renee Claytor
(74) *Attorney, Agent, or Firm* — Wilson Sonsini Goodrich & Rosati

(57) ABSTRACT

Disclosed are pharmaceutical and cosmetic compositions containing aromatic aldehyde compounds. Some of the disclosed compositions are useful as topical therapeutics for treating inflammatory dermatologic conditions. Some of the compositions are useful in transdermal and other systemic dose forms for treating other inflammatory conditions in mammals.

5 Claims, 17 Drawing Sheets

FOREIGN PATENT DOCUMENTS

| | | |
|---|---|---|
| JP | 07002640 | 1/1995 |
| JP | 07242558 | 9/1995 |
| JP | 07 258042 | 10/1995 |
| JP | 07 258074 | 10/1995 |
| JP | 07300412 | 11/1995 |
| JP | 2001106639 | 4/2001 |
| WO | WO 92/09276 | 6/1992 |
| WO | WO 97/47280 | 12/1997 |
| WO | WO 99/03446 | 1/1999 |
| WO | WO 99/06388 | 2/1999 |
| WO | WO 99/07336 | 2/1999 |
| WO | WO 99/22703 | 5/1999 |
| WO | WO 00/38653 | 7/2000 |
| WO | WO 00/74697 | 12/2000 |
| WO | WO 01/28507 | 4/2001 |
| WO | WO 01/34106 | 5/2001 |
| WO | WO 01/76626 | 10/2001 |
| WO | WO 02/083624 | 10/2002 |
| WO | WO 03/000214 | 1/2003 |

OTHER PUBLICATIONS

Batt, D.G. et al, *2-Substituted-1-naphtols as potent 5-lipoxygenase inhibitors with topical antiinflammatory activity*, Journal of Medicinal Chemistry 3.3.(1): 360-370 (1990).

Burton, D. E. et al, *The mechanism of the antibacterial action of phenols and salicylaldehydes. III. Substituted Benzaldehydes*, J Chern Soc 2458-2460 (1964).

Chang, et al., "Benzyloxybenzaldehyde Analogues as Novel Adenyl Cyclase Activators", Bioorg. Med. Chern. Letters, 11(15), pp. 1871-1974 (2001).

Chen et al. "Effects of IH764-3 on chemotactic migration of neutrophils induced by rhIL-8" Chinese Journal Pathophysiology 15:781 (1999) (with English abstract).

Clerici et al. "In vitro immunomodulatory properties of Tucaresol in HIV infection" Clin. Immunology 97:211 (2000).

Farah, et al., "Pharmacologically Active Prenylpropanoids from *Senra incana*", Platnta Medica, 58(1), pp. 14-18 (1992).

Felton, et al., "New Class of Broad Spectrum Antibacterials", TGA Cosmetic J., 2(1), pp. 16-19 (1970).

Glenn "Anomalous biological effects of salicylates and prostaglandins" Agents Actions 9:257 (1979).

Inaoka et al. "Study on hair regrowth promoting substances from the potent herbs, especially *Polyporus umbellatus* F." Tennen Yuki Kagobutsu Toronkai Koen Yoshishu 36:32 (1994) (with English abstract).

Jimenez, M. et al, *Competitive inhibition of mushroon tyrosinase by 4-substituted benzakdehydes*, Journal of Agriculnual and Food Chemistry 4.2(8): 4060-4063 (2001).

Kubo et al. "2-hydroxy-4-methoxybenzaldehyde: A potent tyrosinase inhibitor in african medicinal plants" Planta Med. 65:19 (1999).

Magae et al. "Antitumor protective property of an isoprenoid antibiotic, ascofuranone" Journal of Antibiotics 35:1547 (1982).

Nguyen et al. "Investigation on anti-acute inflammatory action of beta-aminoketone, a derivative of vaniline" Pharmaceutical Journal (Vietnamese) 3:18 (2001) (with complete English translation).

Nomura, M. et al., *Studies on the utilization of cashew nut shell oil. III. Synthesis of 6-[(Z,ii7)-8, 11, 14-pentadecatrienyl] salicylic acid derivatives and their inhibition properties toward tyrosinase or hyaluronidase*, Nippon Kagaku Kajshj 12:986-993 (1995).

Oikawa et al., "Oxidative DNA Damage and Apoptosis Induced by Metabolites of Butylated Hydroxtolune, Biochemical Pharmacology", Elsevier, (1998), vol. 56, pp. 361-370.

Opdyke, D.L.J., *Monographs on fragrance raw materials p-Ethoxybenaldehyde*, Food and Cosmetic Toxicology .18(6):681 (1980).

Reddy et al. "Studies on anti-inflammatory activity of spice principles and dietary n-3 polyunsaturated fatty acids on carrageenan-induced inflammation in rats" Ann. Nutr. Metab. 38:349-58 (1994).

Remington's Pharmaceutical Sciences, 18th Ed., Part 8, "Pharmaceutical Preparations and their Manufacture" pp. 1435-1693, (1990), Mack Publishing Company, Easton, Pennsylvania.

Remington: The Science and Practice of Pharmacy, 20th Edition, (2000) Published by the Philadelphia College of Pharmacy and Science, Edited by Alfonso R. Gennaro et al., pp. 836-844 and 917-918.

Van Den Worm et al., "Effects of Methoxylation of Apocyanin and Analogs on the inhibition of Reactive Oxygen Species Production by Stimulated Human Neutrophils", Eur. J. Pharmacal., 433(2-3), pp. 225-230 (2001).

Whitehouse et al "Alternatives to aspirin, derived from biological sources" Agents Actions Suppl. 1:43-57 (1977).

\* cited by examiner

FIGURE 4
A)
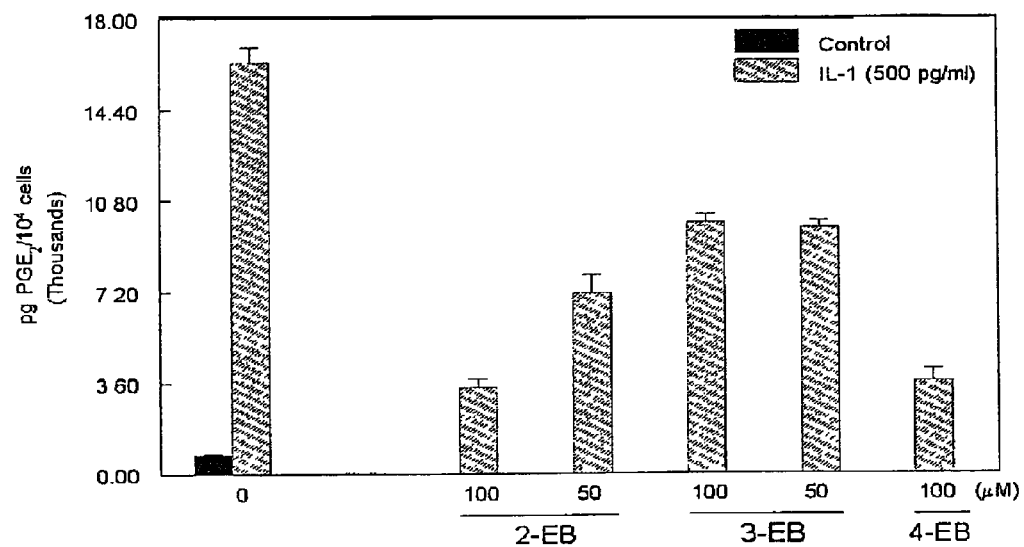
B)
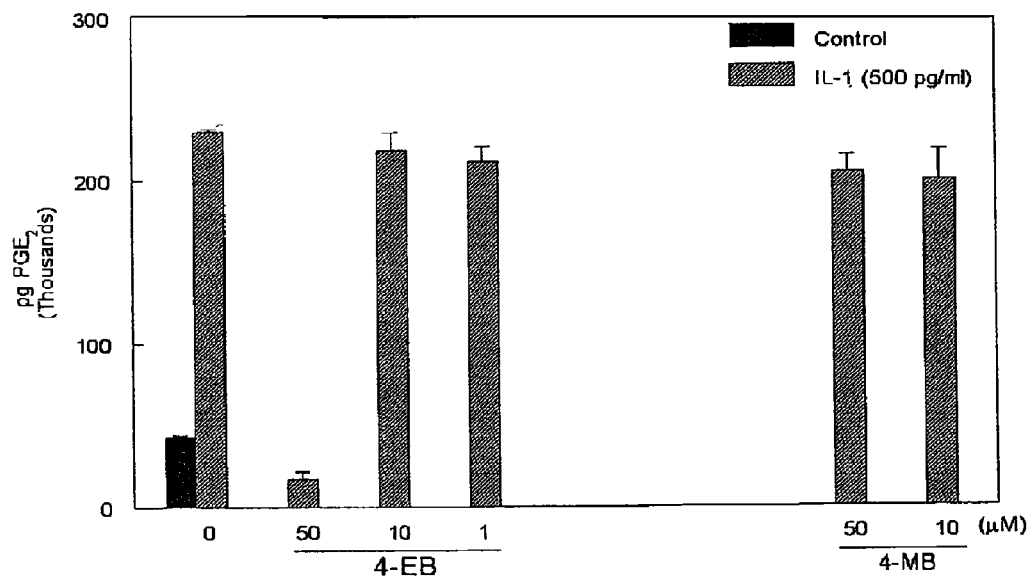

FIGURE 6

| Drug | (μM) | Ultraviolet Light | | | Fibroblasts | | | | |
|---|---|---|---|---|---|---|---|---|---|
| | | PGE-2 | IL-1 | IL-6 | IL-8 | PGE-2 | IL-6 | IL-1 IL-8 | MMP-1 |
| CX-1<br>2,4 Diethoxy Benzaldehyde | 1<br>10<br>100 | -<br>-<br>- | -<br>-<br>- | -<br>-<br>- | -<br>-<br>- | -<br>-<br>Cell Death | -<br>-<br>- | -<br>-<br>Cell Death | -<br>-<br>Cell Death |
| CX-2<br>Benzaldehyde Dimethyl Acetal | 1<br>10<br>100 | -<br>-<br>- | -<br>-<br>- | -<br>-<br>- | -<br>-<br>- | -<br>12<br>- | -<br>-<br>- | -<br>NE<br>- | -<br>NE<br>- |
| CX-3<br>2,4,5 Triethoxy Benzaldehyde | 1<br>10<br>100 | -<br>-<br>- | -<br>-<br>- | -<br>-<br>- | -<br>-<br>- | -<br>-<br>Cell Death | -<br>-<br>- | -<br>-<br>Cell Death | -<br>-<br>Cell Death |
| CX-4<br>3,5-di-tert-butyl-4-hydroxy Benzaldehyde | 1<br>10<br>100 | -<br>>100<br>>100 | -<br>NI<br>NI | -<br>63<br>64 | -<br>47<br>67 | -<br>NE<br>22<br>100 | -<br>NE<br>62<br>54 | -<br>-<br>20 | -<br>-<br>- |
| CX-5<br>2-Ethoxy Benzaldehyde | 1<br>10<br>100 | -<br>97<br>>100 | -<br>-<br>- | -<br>-<br>- | -<br>74<br>>100 | -<br>59<br>77 | -<br>31<br>49 | -<br>29<br>26 | -<br>-<br>- |
| CX-6<br>2-Propoxy Benzaldehyde | 1<br>10<br>100 | -<br>-<br>- | -<br>-<br>- | -<br>-<br>- | -<br>-<br>- | -<br>78<br>93 | -<br>-<br>- | -<br>-<br>- | -<br>-<br>- |
| CX-7<br>3-Dodecycloxy Benzaldehyde | 1<br>10<br>100 | -<br>-<br>- | -<br>-<br>- | -<br>-<br>- | -<br>-<br>- | -<br>75<br>- | -<br>5<br>- | -<br>NE<br>- | -<br>NE<br>- |
| CX-8<br>3 Ethoxy 4 Hydroxy Benzaldehyde | 1<br>10<br>100 | -<br>-<br>- | -<br>-<br>- | -<br>-<br>- | -<br>-<br>- | 12<br>31<br>84 | 36<br>24<br>33 | 4<br>3<br>20 | NE<br>NE<br>NE |
| CX-9<br>3-Benzyloxy-4,5-Dimethoxy Benzaldehyde | 1<br>10<br>100 | -<br>-<br>- | -<br>-<br>- | -<br>-<br>- | -<br>-<br>- | -<br>78<br>- | -<br>43<br>- | -<br>48<br>- | -<br>NE<br>- |
| CX-10<br>3-Ethoxy Benzaldehyde | 1<br>10<br>100 | -<br>32<br>58 | -<br>-<br>- | -<br>45<br>67 | -<br>30<br>52 | -<br>43<br>41 | -<br>51<br>52 | -<br>29<br>35 | -<br>-<br>- |
| CX-11<br>3,5-Dihydroxy Benzaldehyde | 1<br>10<br>100 | -<br>-<br>- | -<br>-<br>- | -<br>-<br>- | -<br>-<br>- | -<br>65<br>- | -<br>16<br>- | -<br>NE<br>- | -<br>6<br>- |
| CX-12<br>4-Methoxy Benzaldehyde | 1<br>10<br>100 | -<br>-<br>- | -<br>-<br>- | -<br>-<br>- | -<br>-<br>- | -<br>70<br>- | -<br>8<br>- | -<br>1<br>- | -<br>10<br>- |

FIGURE 6 (continued)

| Drug | (µM) | Ultraviolet Light | | | | Fibroblasts | | | | |
|---|---|---|---|---|---|---|---|---|---|---|
| | | PGE-2 | IL-1 | IL-6 | IL-8 | PGE-2 | IL-6 | IL-1 | | MMP-1 |
| | | | | | | | | IL-8 | | |
| CX-13<br>4-Benzyloxy Benzaldehyde | 1<br>10<br>100 | -<br>-<br>- | -<br>-<br>- | -<br>-<br>- | -<br>-<br>- | -<br>-<br>60 | -<br>-<br>37 | -<br>-<br>21 | -<br>-<br>NE | -<br>-<br>- |
| CX-14<br>4-Acetoxy-3,5-Dimethoxy Benzaldehyde | 1<br>10<br>100 | -<br>-<br>- | -<br>-<br>- | -<br>-<br>- | -<br>-<br>- | -<br>-<br>97 | -<br>-<br>- | -<br>-<br>24 | -<br>-<br>NE | |
| CX-15<br>4-Hydroxy-3,5-Dimethoxy Benzaldehyde | 1<br>10<br>100 | -<br>-<br>- | -<br>-<br>- | -<br>-<br>- | -<br>-<br>- | NE<br>NE<br>90 | -<br>-<br>48 | -<br>-<br>39 | -<br>-<br>NE | |
| CX-16<br>4-Allyloxy Benzaldehyde | 1<br>10<br>100 | -<br>16<br>62 | -<br>-<br>- | -<br>-<br>- | -<br>-<br>- | 13<br>94<br>>100 | -<br>-<br>29 | 43<br>30<br>3 | -<br>-<br>NE | |
| CX-17<br>4-tert-pentyl Benzaldehyde | 1<br>10<br>100 | -<br>-<br>- | -<br>-<br>- | -<br>-<br>- | -<br>-<br>- | -<br>-<br>18 | -<br>-<br>- | -<br>-<br>NE | -<br>-<br>NE | |
| CX-18<br>Benzaldehyde | 1<br>10<br>100 | -<br>-<br>- | -<br>-<br>- | -<br>-<br>- | -<br>-<br>- | -<br>44<br>50 | -<br>-<br>- | -<br>45<br>44 | -<br>20<br>28 | |
| CX-19<br>Benzyl Alcohol | 1<br>10<br>100 | -<br>-<br>- | -<br>-<br>- | -<br>-<br>- | -<br>-<br>- | -<br>-<br>12 | -<br>-<br>30 | -<br>-<br>29 | -<br>-<br>NE | |
| CX-20<br>4-Ethyl Benzaldehyde | 1<br>10<br>100 | -<br>-<br>- | -<br>-<br>- | -<br>-<br>- | -<br>-<br>- | -<br>-<br>9 | -<br>-<br>- | -<br>-<br>NE | -<br>-<br>NE | |
| CX-21<br>4-Ethoxy Benzaldehyde | 1<br>10<br>100 | -<br>NE<br>>100 | -<br>90<br>NI | -<br>>100<br>>100 | -<br>NE<br>44 | 3<br>38<br>80 | NE<br>13<br>15 | 8<br>8<br>9 | NE<br>NE<br>NE | |
| CX-22<br>4-Propoxy Benzaldehyde | 1<br>10<br>100 | -<br>76<br>91 | -<br>-<br>- | -<br>-<br>- | -<br>-<br>- | NE<br>79<br>>100 | -<br>-<br>- | NE<br>NE<br>10 | -<br>-<br>NE | |
| CX-23<br>4-Butoxy Benzaldehyde | 1<br>10<br>100 | -<br>-<br>- | -<br>-<br>- | -<br>-<br>- | -<br>-<br>- | 21<br>86<br>95 | -<br>-<br>- | NE<br>NE<br>NE | -<br>-<br>- | |
| CX-24<br>4-Pentyloxy Benzaldehyde | 1<br>10<br>100 | -<br>82<br>83 | -<br>-<br>- | -<br>-<br>- | -<br>-<br>- | 60<br>95<br>100 | 47<br>61<br>58 | 40<br>55<br>44 | 31<br>18<br>21 | |
| CX-25<br>4-Hexyloxy Benzaldehyde | 1<br>10<br>100 | -<br>97<br>>100 | -<br>-<br>- | -<br>-<br>- | -<br>-<br>- | 34<br>86<br>97 | -<br>-<br>- | 40<br>15<br>NE | -<br>-<br>NE | |

FIGURE 7

| Drug | (µM) | Keratinocytes Ultraviolet Light | | | | | | Phorbol Ester | | | | | |
|---|---|---|---|---|---|---|---|---|---|---|---|---|---|
| | | PGE-2 | IL-1 | IL-6 | IL-8 | TNF-α | MMP-1 | PGE-2 | IL-1 | IL-6 | IL-8 | TNF-α | MMP-1 |
| CX-1 2,4 Diethoxy Benzaldehyde | 1 | - | - | - | - | - | - | - | - | - | - | - | - |
| | 10 | - | - | - | - | - | - | - | - | - | - | - | - |
| | 100 | - | - | - | - | - | - | - | - | - | - | - | - |
| CX-2 Benzaldehyde Dimethyl Acetal | 1 | - | - | - | - | - | - | - | - | - | - | - | - |
| | 10 | - | - | - | - | - | - | - | - | - | - | - | - |
| | 100 | - | - | - | - | - | - | 100 | NE | NE | NE | NE | NE |
| CX-3 2,4,5 Triethoxy Benzaldehyde | 1 | - | - | - | - | - | - | - | - | - | - | - | - |
| | 10 | - | - | - | - | - | - | - | - | - | - | - | - |
| | 100 | - | - | - | - | - | - | - | - | - | - | - | - |
| CX-4 3,5-di-tert-butyl-4-hydroxy Benzaldehyde | 1 | - | - | - | - | - | - | - | - | - | - | - | - |
| | 10 | 24 | NE | 65 | NE | - | - | 94 | - | NE | 28 | - | - |
| | 100 | 68 | Crystals | 66 | NE | - | - | Crystals | - | Crystals | Crystals | - | - |
| CX-5 2-Ethoxy Benzaldehyde | 1 | - | - | - | - | - | - | - | - | - | - | - | - |
| | 10 | 16 | NE | 54 | NE | - | - | 55 | - | NE | NE | - | - |
| | 100 | 33 | NE | 78 | NE | - | - | 91 | - | 54 | 23 | - | - |
| CX-6 2-Propoxy Benzaldehyde | 1 | - | - | - | - | - | - | - | - | - | - | - | - |
| | 10 | - | - | - | - | - | - | - | - | - | - | - | - |
| | 100 | - | - | - | - | - | - | - | - | - | - | - | - |
| CX-7 3-Dodecycloxy Benzaldehyde | 1 | - | - | - | - | - | - | - | - | - | - | - | - |
| | 10 | - | - | - | - | - | - | - | - | - | - | - | - |
| | 100 | - | - | - | - | - | - | - | - | - | - | - | - |
| CX-8 3 Ethoxy 4 Hydroxy Benzaldehyde | 1 | - | - | - | - | - | - | - | - | - | - | - | - |
| | 10 | - | - | - | - | - | - | - | - | - | - | - | - |
| | 100 | - | - | - | - | - | - | 58 | 58 | NE | NE | 7 | NE |
| CX-9 3-Benzyloxy-4,5-Dimethoxy Benzaldehyde | 1 | - | - | - | - | - | - | - | - | - | - | - | - |
| | 10 | - | - | - | - | - | - | - | - | - | - | - | - |
| | 100 | - | - | - | - | - | - | - | - | - | - | - | - |
| CX-10 3-Ethoxy Benzaldehyde | 1 | - | - | - | - | - | - | - | - | - | - | - | - |
| | 10 | 21 | NE | 53 | NE | - | - | 74 | - | NE | NE | - | - |
| | 100 | 30 | NE | 57 | NE | - | - | 85 | - | 71 | 9 | - | - |
| CX-11 3,5-Dihydroxy Benzaldehyde | 1 | - | - | - | - | - | - | - | - | - | - | - | - |
| | 10 | - | - | - | - | - | - | - | - | - | - | - | - |
| | 100 | - | - | - | - | - | - | - | - | - | - | - | - |
| CX-12 4-Methoxy Benzaldehyde | 1 | - | - | - | - | - | - | - | - | - | - | - | - |
| | 10 | NE | NE | NE | NE | - | - | - | - | - | - | - | - |
| | 100 | 88 | NE | 78 | NE | - | - | - | - | - | - | - | - |

FIGURE 7 (continued)

| Drug | (μM) | Keratinocytes ||||||||||||
|---|---|---|---|---|---|---|---|---|---|---|---|---|
| | | Ultraviolet Light |||||| Phorbol Ester ||||||
| | | PGE-2 | IL-1 | IL-6 | IL-8 | TNF-α | MMP-1 | PGE-2 | IL-1 | IL-6 | IL-8 | TNF-α | MMP-1 |
| CX-13 4-Benzyloxy Benzaldehyde | 1 | - | - | - | - | - | - | - | - | - | - | - | - |
| | 10 | - | - | - | - | - | - | - | - | - | - | - | - |
| | 100 | - | - | - | - | - | - | - | - | - | - | - | - |
| CX-14 4-Acetoxy-3,5-Dimethoxy Benzaldehyde | 1 | - | - | - | - | - | - | - | - | - | - | - | - |
| | 10 | - | - | - | - | - | - | - | - | - | - | - | - |
| | 100 | - | - | - | - | - | - | - | - | - | - | - | - |
| CX-15 4-Hydroxy-3,5-Dimethoxy Benzaldehyde | 1 | - | - | - | - | - | - | - | - | - | - | - | - |
| | 10 | - | - | - | - | - | - | - | - | - | - | - | - |
| | 100 | - | - | - | - | - | - | - | - | - | - | - | - |
| CX-16 4-Allyloxy Benzaldehyde | 1 | - | - | - | - | - | - | - | - | - | - | - | - |
| | 10 | - | - | - | - | - | - | 36 | >100 | 26 | 12 | 30 | 17 |
| | 100 | - | - | - | - | - | - | - | - | - | - | - | - |
| CX-17 4-tert-pentyl Benzaldehyde | 1 | - | - | - | - | - | - | - | - | - | - | - | - |
| | 10 | - | - | - | - | - | - | - | - | - | - | - | - |
| | 100 | - | - | - | - | - | - | - | - | - | - | - | - |
| CX-18 Benzaldehyde | 1 | - | - | - | - | - | - | - | - | - | - | - | - |
| | 10 | - | - | - | - | - | - | - | - | - | - | - | - |
| | 100 | - | - | - | - | - | - | - | - | - | - | - | - |
| CX-19 Benzyl Alcohol | 1 | - | - | - | - | - | - | - | - | - | - | - | - |
| | 10 | - | - | - | - | - | - | - | - | - | - | - | - |
| | 100 | - | - | - | - | - | - | - | - | - | - | - | - |
| CX-20 4-Ethyl Benzaldehyde | 1 | - | - | - | - | - | - | NE | NE | NE | NE | NE | NE |
| | 10 | 45 | 15 | 84 | 45 | - | - | 52 | - | NE | 11 | 3 | - |
| | 100 | 68 | NE | 77 | 25 | - | - | 82 | 53 | NE | 7 | 6 | NE |
| CX-21 4-Ethoxy Benzaldehyde | 1 | - | - | - | - | - | - | 89 | - | NE | 5 | - | NE |
| | 10 | - | - | - | - | - | - | - | - | - | - | - | - |
| | 100 | - | - | - | - | - | - | - | - | - | - | - | - |
| CX-22 4-Propoxy Benzaldehyde | 1 | - | - | - | - | - | - | - | - | - | - | - | - |
| | 10 | - | - | - | - | - | - | - | - | - | - | - | - |
| | 100 | - | - | - | - | - | - | - | - | - | - | - | - |
| CX-23 4-Butoxy Benzaldehyde | 1 | - | - | - | - | - | - | - | - | - | - | - | - |
| | 10 | - | - | - | - | - | - | - | - | - | - | - | - |
| | 100 | - | - | - | - | - | - | - | - | - | - | - | - |
| CX-24 4-Pentyloxy Benzaldehyde | 1 | - | - | - | - | - | - | - | - | - | - | - | - |
| | 10 | >100 | 12 | 100 | 77 | 90 | >100 | >100 | >100 | 37 | 6 | 26 | - |
| | 100 | - | - | - | - | - | - | - | - | - | - | - | - |
| CX-25 4-Hexyloxy Benzaldehyde | 1 | - | - | - | - | - | - | - | - | - | - | - | - |
| | 10 | 98 | NE | 100 | >100 | >100 | >100 | NE | - | 74 | 67 | 87 | 80 |
| | 100 | - | - | - | - | - | - | - | - | - | - | - | - |

FIGURE 11A  Percent Inhibition of UV Induced PGE-2 in Fibroblasts
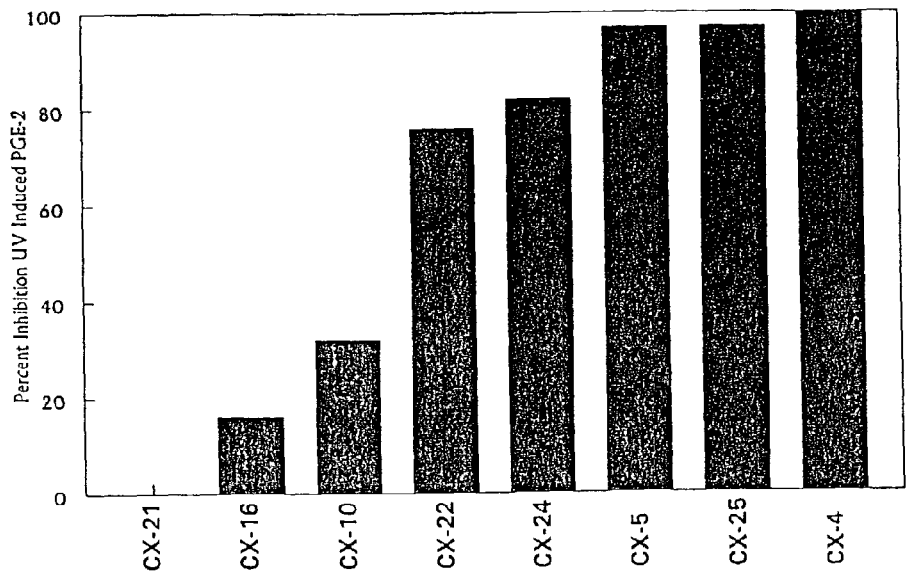
FIGURE 11B  Percent Inhibition of UV Induced PGE-2 in Fibroblasts
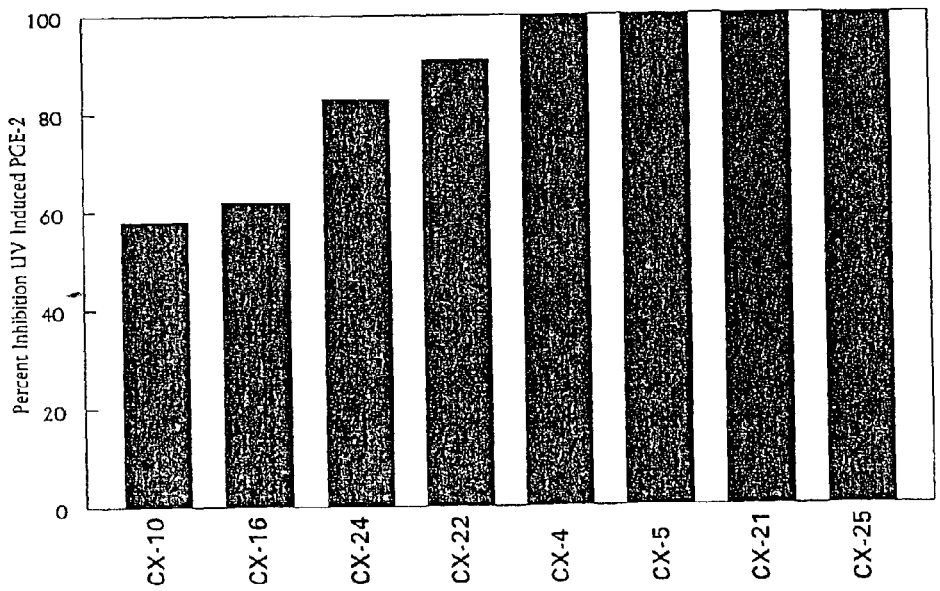

FIGURE 13A  Percent Inhibition of UV Induced IL-8 in Keratinocytes
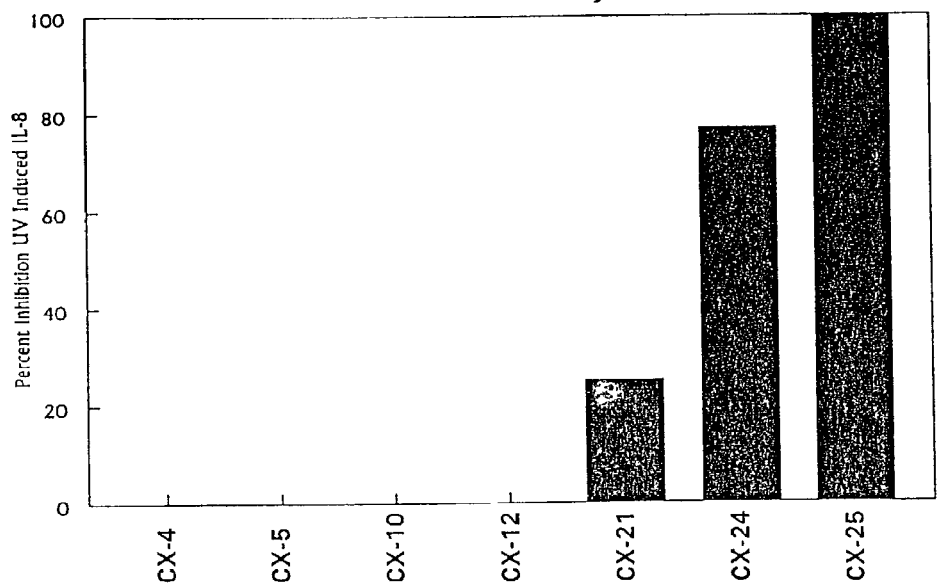
FIGURE 13B  Percent Inhibition of TPA Induced PGE-2 in Keratinocytes
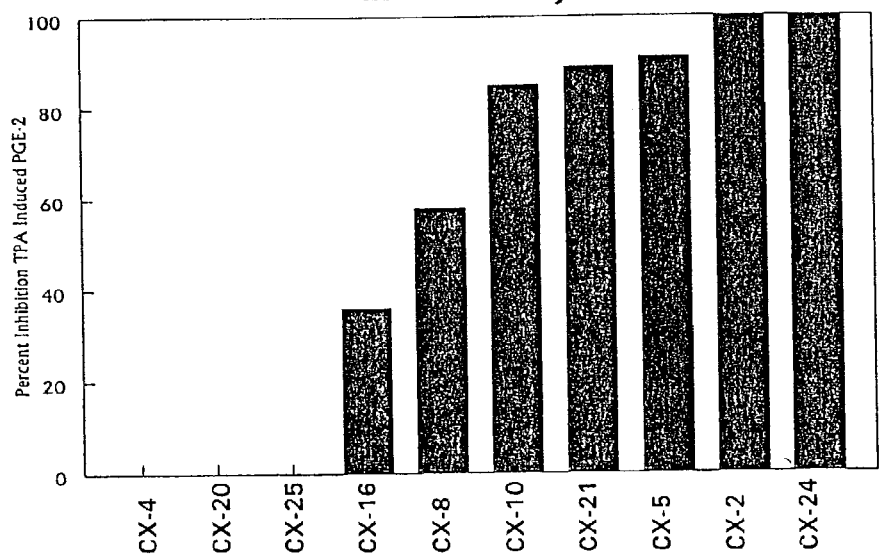

FIGURE 15A Effect of Test Lotion on Rosacea at 4 Weeks
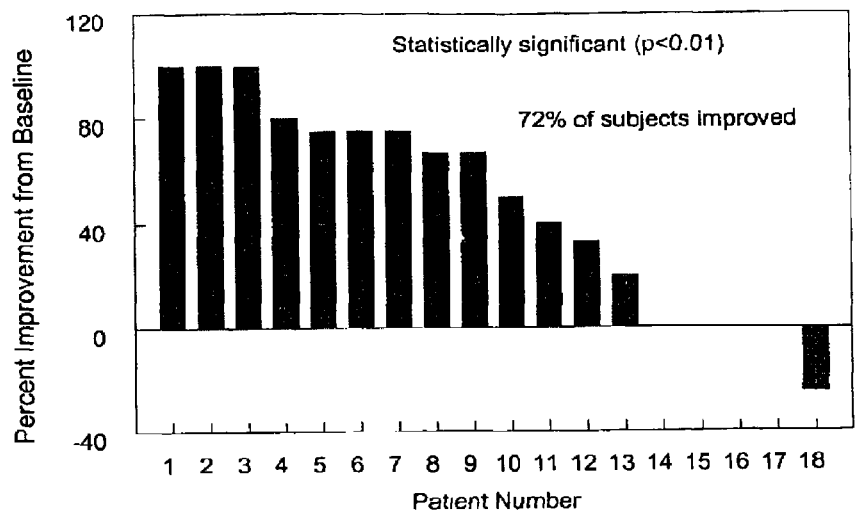
FIGURE 15B Effect of Control Lotion on Rosacea at 4 Weeks
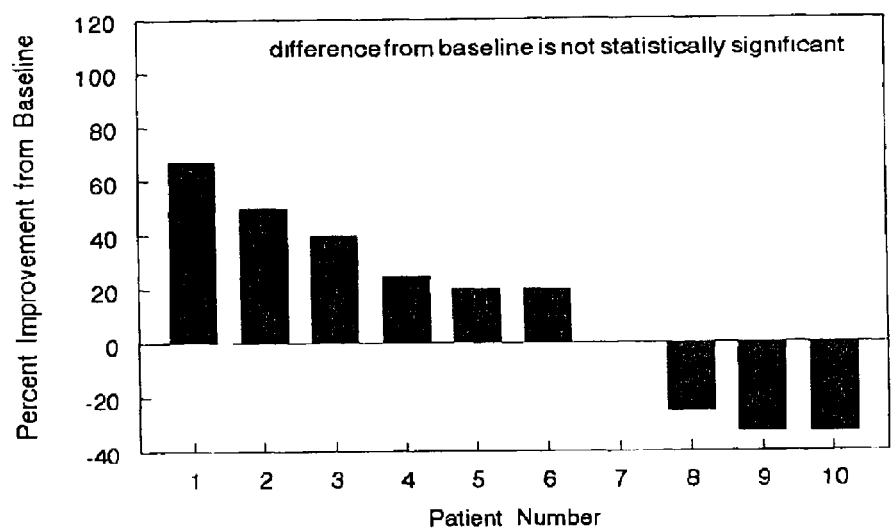

COMPOSITIONS CONTAINING AROMATIC ALDEHYDES AND THEIR USE IN TREATMENTS

CROSS-REFERENCE TO RELATED APPLICATIONS

This application is a continuation of U.S. patent application Ser. No. 10/223,073, which was filed on Aug. 15, 2002, and which claims priority under 35 U.S.C. §119(e) to U.S. Provisional Application Ser. No. 60/332,277, which was filed on Nov. 16, 2001, and to U.S. Provisional Application Ser. No. 60/346,049, which was filed on Jan. 4, 2002, and to U.S. Provisional Application Ser. No. 60/368,518, which was filed on Apr. 1, 2002, and to U.S. Provisional Application Ser. No. 60/384,589, which was filed on May 30, 2002, the disclosures of which are incorporated herein in their entirety.

BACKGROUND OF THE INVENTION

1. Field of the Invention

This invention relates to aromatic aldehydes and their use as active ingredients in cosmetics and pharmaceuticals. More particularly, it concerns such aldehydes and their use in cosmetics and as topical, transdermal or systemic pharmaceuticals.

2. State of the Art

This invention involves the use of aromatic aldehydes. Many aromatic aldehydes are known materials that commonly find use as chemical intermediates. Some aromatic aldehydes are components of natural products as well.

The present invention uses these aldehydes as active ingredients in pharmaceuticals and cosmetics. While the invention contemplates that these aldehyde materials can find application as systemic agents against inflammatory conditions when delivered transdermally or orally or by injection, at this time their preferred uses are as components of topical cosmetic and pharmaceutical compositions used to treat a wide range of dermatological conditions ranging from dermatitis and U.V.—induced inflammation through psoriasis and acne.

Therapies used in the past to deal with conditions such as eczema and psoriasis have included the use of simple emollients. Topical steroids ranging from mild agents such as hydrocortisone (1%) through more potent materials such as clobetasol propionate (0.05%) have been indicated with the common inflammatory dermatoses. In addition, corticosteroids and immunosuppresents have been used to treat skin conditions. Vitamin D and its derivatives such as calcipotrial and tacolcitol and vitamin A and other retinoids have been used to treat dermatological problems. The vitamin D materials are used to treat acne.

In addition to those directly topical therapies, it is well known that many materials pass through the skin and enter the systemic circulation when placed on the skin. The line between "topical" and this so called "transdermal" administration of drugs is a fuzzy one and many therapies heretofore have had both topical and transdermal aspects.

These therapies are not without their limitations. Emollients are very temporary and must be repeatedly renewed. Topical steroid use is associated with thinning skin, bruising, and rashes as well as serious systemic side effects such as development of Cushing's Syndrome.

The vitamin D materials often pass transdermally and can have unexpected effects on the user's systemic calcium metabolism. The retinoids are reported to cause acne in some cases and to produce teratogenic effects if absorbed transdermally during pregnancy.

It is clear that there is a need for additional topical compositions which can effectively treat dermatological conditions. It would be highly desirable if these compositions could also treat and optionally transdermally or otherwise systemically treatable inflammatory conditions and avoid some or all of the problems associated with therapies now in use.

SUMMARY OF THE INVENTION

It has now been found that a group of aromatic aldehydes are effective topical agents against inflammation-related dermatological conditions. These aldehydes also appear to be delivered to a measurable extent transdermally and thus to potentially achieve systemic and/or localized anti-inflammatory effects within the body. In view of these findings, it further appears that these aldehydes can be effective against other inflammatory conditions when administered by other systemic routes.

In one of its composition aspects, this invention is directed to topical pharmaceutical and cosmetic compositions containing a pharmaceutically-acceptable topical carrier and one or more aromatic aldehyde compounds. These aromatic aldehydes include materials of Formula I, as well as protected versions, that is, acetals as in Formula II, and hemiacetals as in Formula III:

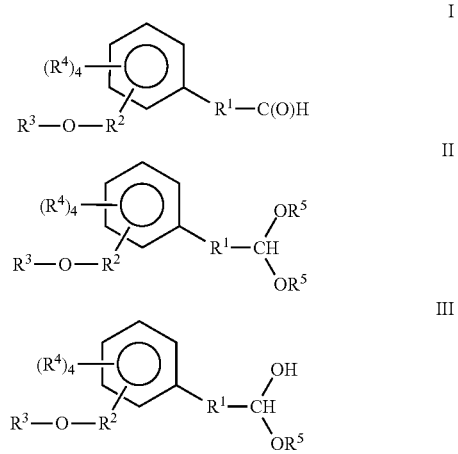

wherein $R^1$ is a carbon-carbon single bond or a straight chain or branched chain alkylene;

$R^2$ is a carbon-oxygen single bond or a straight chain or branched chain alkylene;

$R^3$ is a straight chain or branched chain alkyl, a cycloalkyl, an alkcycloalkyl, an alkenyl, an aryl or an aralkyl; and each $R^4$ is independently selected from the group consisting of hydrogen, alkyl, substituted alkyl, alkcycloalkyl, cycloalkyl, alkoxy, alkcycloalkoxy, cycloalkoxy, acyl acyloxy and halogen; and each $R^5$ is independently alkyl, or in the case of the acetals of Formula II, the two $R^5$s together with the atoms to which they are attached form a heterocycloalkyl;

subject to the proviso that the compound of Formula I is neither
2-4-diethoxybenzaldehyde, nor
2,4,5-triethoxybenzaldehyde.

In another of its composition aspects, this invention is directed to pharmaceutical compositions for topical, transdermal or other systemic administration containing a pharmaceutically-acceptable carrier and one or more of the aromatic aldehyde compounds of Formula I, II or III, excluding formulations where the compound of Formula I is 4-methoxybenzaldehyde for use systemic administration.

In one of its method aspects, this invention is directed to a method for treating a patient with a dermatological disease which method comprises topically administering to said patient a pharmaceutical composition comprising a pharmaceutically acceptable topical carrier and an effective dermatological disease-treating amount of a compound of Formula I, II or III above.

In another one of its method aspects, this invention is directed to a method for treating a dermatological condition, which method comprises topically applying to a human a cosmetic composition comprising a pharmaceutically acceptable topical carrier and an effective amount of a compound of Formula I, II or III above.

In still another of its method aspects, this invention is directed to a method for treating a patient with an inflammatory disease which method comprises systemically administering to said patient a pharmaceutical composition comprising a pharmaceutically acceptable carrier and an effective inflammatory disease-treating amount of a compound of Formula I, II or III above, excluding the compound 4-methoxybenzaldehyde.

In yet another of its method aspects, this invention is directed to a method for treating a human with an inflammatory condition which method comprises topically applying to said human a pharmaceutical composition comprising a pharmaceutically acceptable carrier and an effective amount of a compound of Formula I, II or III above.

DETAILED DESCRIPTION OF THE INVENTION

Brief Description of the Drawing

FIG. 3 and FIGS. 4A and 4B: Bar graphs which show the effects of aldehydes employed in the compositions of this invention on interleukin 1 "1L-1"-induced prostaglandin E2 "$PGE_2$" expression in dermal fibroblasts.

FIG. 6: A table which shows the effects of aldehydes employed in the compositions of this invention and other related compounds on expression levels of varius proteins in fibroblasts challenged with 1L-1 or UV light.

FIG. 7: A table which shows the effects of aldehydes employed in the compositions of this invention and other related compounds on expression levels of varius proteins in keratinocytes challenged with TPA or UV light.

FIGS. 8A, 8B, 9A, 9B, 10A, 10B, 11A and 11B: Bar graphs of data tabulated in FIG. 6.

FIGS. 12A, 12B, 13A, 13B, 14A and 14B: Bar graphs of data tabulated in FIG. 7.

FIGS. 15A and 15B: Bar graphs of data obtained in an in vivo test of the lotion formulation of Example 8.

DEFINITIONS

Figure 1:
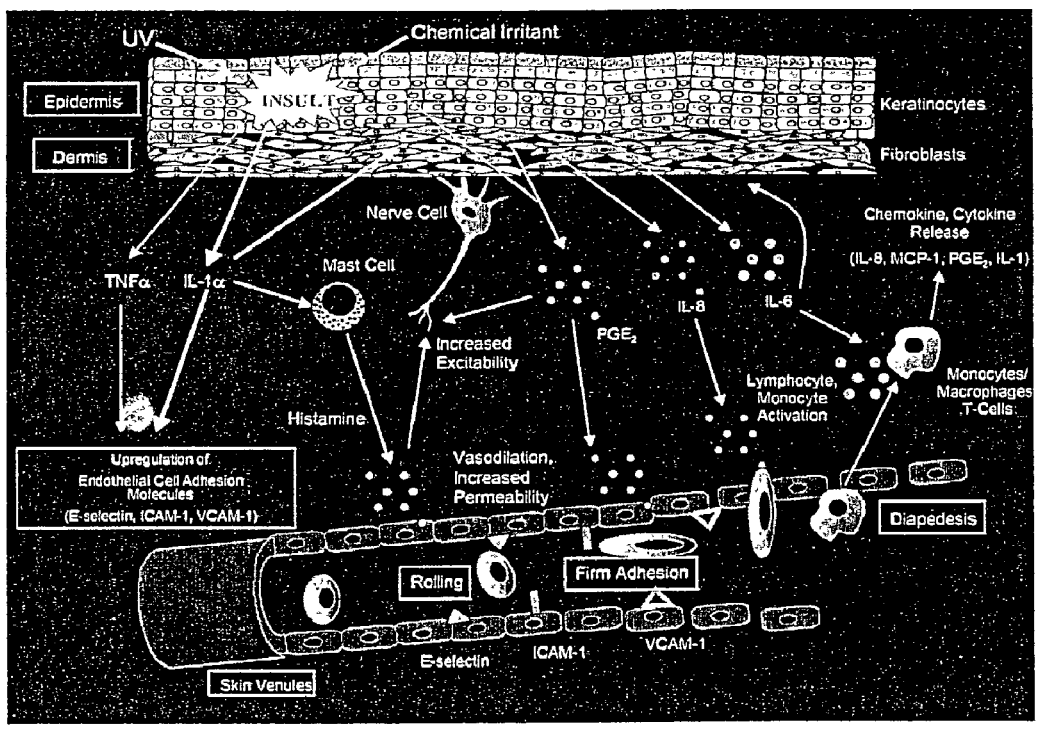
FIG. 1: A schematic diagram illustrating inflammatory processes in the skin and showing the relationship of inflammation to the release of various proteins.

When describing the aromatic aldehyde compounds employed in the cosmetic and pharmaceutical compositions and methods of this invention as well as the compositions and methods themselves, the following terms have the following meanings:

"Acyl" refers to the group —C(O)R where R is hydrogen, alkyl or aryl. When R is hydrogen this is a "formyl", when R is $CH_3$ this is "acetyl".

"Acyloxy" refers to the group —O-Acyl.

"Alkyl" refers to monovalent saturated aliphatic hydrocarbon groups preferably having from 1 to about 20 carbon atoms, more preferably from 1 to 12, even more preferably 1 to 8 carbon atoms. This term is exemplified by groups such as methyl, ethyl, n-propyl, isopropyl, n-butyl, isobutyl, tert-butyl, n-hexyl, n-octyl, tert-octyl and the like. The term "lower alkyl" refers to alkyl groups having 1 to 6 carbon atoms and especially 1 to 4 carbon atoms.

"Substituted alkyl" refers to an alkyl group, preferably of from 1 to about 20 carbon atoms, having from 1 to 5 substituents, and preferably 1 to 3 substituents, selected from the group consisting of alkoxy, cycloalkyl, cycloalkoxy, acyl, aminoacyl, amino, aminocarbonyl, cyano, halogen, hydroxyl, carboxyl, keto, thioketo, alkoxycarbonyl, thiol, thioalkoxy, aryl, aryloxy, nitro, —$OSO_3H$ and pharmaceutically acceptable salts thereof, —SO-alkyl, —SO-substituted alkyl, —$SO_2$-aryl, —$SO_2$-alkyl, —$SO_2$-substituted alkyl, —$SO_2$-aryl, and mono- and di-alkylamino, mono- and di-arylamino, and unsymmetric di-substituted amines having different substituents selected from alkyl, substituted alkyl and aryl.

"Alkenyl" refers to monovalent unsaturated aliphatic hydrocarbon groups having from 1 to 20 carbon atoms and preferably 1 to 6 carbon atoms and 1 to 2 and especially 1 olefinic unsaturation.

"Alkylene" refers to divalent saturated aliphatic hydrocarbon groups preferably having from 1 to 20 carbon atoms and more preferably 1 to 6 carbon atoms which can be straight chain or branched. This term is exemplified by groups such as methylene (—$CH_2$—), ethylene (—$CH_2CH_2$—), the propylene isomers (e.g., —$CH_2CH_2CH_2$— and —$CH(CH_3)CH_2$—) and the like.

"Alkcycloalkyl" refers to -alkylene-cycloalkyl groups preferably having from 1 to 20 carbon atoms in the alkylene moiety and from 3 to 8 carbon atoms in the cycloalkyl moiety. Such alkcycloalkyl groups are exemplified by —$CH_2$-cyclopropyl, —$CH_2$-cyclopentyl, —$CH_2CH_2$-cyclohexyl, and the like.

"Alkcycloalkoxy" refers to —O-alkylene-cycloalkyl groups preferably having from 1 to 20 carbon atoms in the alkylene moiety and from 3 to 8 carbon atoms in the cycloalkyl moiety. Such alkcycloalkoxy groups are exemplified by —$OCH_2$-cyclopropyl, —$OCH_2$-cyclopentyl, —$OCH_2CH_2$-cyclohexyl, and the like.

"Alkoxy" refers to the group "alkyl-O—". Preferred alkoxy groups include, by way of example, methoxy, ethoxy, n-propoxy, isopropoxy, n-butoxy, tert-butoxy, sec-butoxy, n-pentyloxy, n-hexyloxy, 1,2-dimethylbutoxy, and the like.

"Alkoxycarbonyl" refers to the group —C(O)OR where R is alkyl.

"Aminocarbonyl" refers to the group —C(O)NRR where each R is independently hydrogen or alkyl.

"Aminoacyl" refers to the group —NRC(O)R where each R is independently hydrogen or alkyl.

"Aryl" refers to an unsaturated aromatic carbocyclic group of from 6 to 14 carbon atoms having a single ring (e.g., phenyl) or multiple condensed rings (e.g., naphthyl or anthryl). Preferred aryls include phenyl, naphthyl and the like. Unless otherwise constrained by the definition for the individual substituent, such aryl groups can optionally be substituted with from 1 to 3 substituents selected from the group consisting of alkyl, alkoxy, alkaryloxy, alkenyl, alkynyl, amino, aminoacyl, aminocarbonyl, alkoxycarbonyl, aryl, carboxyl, cycloalkoxy, cyano, halo, hydroxy, nitro, trihalomethyl, thioalkoxy, and the like.

"Aralkyl" refers to the group "alkylene-aryl" and is most typically benzyl.

"Aryloxy" refers to —O-aryl groups wherein "aryl" is as defined above.

"Carboxyl" refers to the group —C(O)OH.

"Cyano" refers to the group —CN.

"Cycloalkyl" refers to cyclic alkyl groups of from 3 to 20 carbon atoms having a single cyclic ring or multiple condensed rings, including fused and bridged ring systems, which can be optionally substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, or multiple ring structures such as adamantanyl, and the like.

"Cycloalkoxy" refers to —O-cycloalkyl groups. Such cycloalkoxy groups include, by way of example, cyclopentyloxy, cyclohexyloxy and the like.

"Heterocycloalkyl" refers to cyclic groups of from 2 to 10 carbon atoms and 1, 2 or 3 heteroatoms selected from nitrogen, sulfur, or phosphorous, especially oxygen, for example. The ring can be optionally substituted with from 1 to 3 alkyl groups. Such heterocycloalkyl groups include, by way of example, single ring structures such as tetrahydrofuran, 1,4 dioxacyclopentanyl, dioxane, pyrrolidine, tetrahydrothiophene, and the like.

"Ionizing radiation" refers to any radiation that ionizes the atoms or molecules of matter. It may consist of particles (such as electrons) or it may be electromagnetic (ultraviolet radiation; X-rays; gamma radiation). Ionizing radiation occurs naturally, for example as a component of sunlight, and is emitted by radioactive substances. It is also produced artificially in X-ray machines, particle accelerators, nuclear reactors, etc.

"Isolated", when used to define the state of purity of the aromatic aldehyde compounds used in the practice of this invention, means that the aromatic aldehyde has been substantially freed of (i.e at least about 90% and especially at least about 95% freed of) or separated from related feedstocks, co-products, or in the case of naturally-occurring mixtures, related materials with which the aldehyde appears in nature.

"Pharmaceutically-acceptable topical carrier" and equivalent terms refer to an inactive liquid or cream vehicle capable of suspending or dissolving the aromatic aldehyde and having the properties of being nontoxic and noninflammatory when applied to the skin. This term is specifically intended to encompass carrier materials approved for use in topical cosmetics. Representative carriers include water, oils, both vegetable and mineral, cream bases, lotion bases, ointment bases and the like. These bases include suspending agents, thickeners, penetration enhancers, and the like. Their formulation is well known to those in the art of cosmetics and topical pharmaceuticals. Additional information concerning carriers can be found in Part 8 of *Remington's Pharmaceutical Sciences,* 17th edition, 1985, Mack Publishing Company, Easton, Pa., which is incorporated herein by reference.

"Therapeutically effective dose" means a dose of a composition of this invention which, when applied topically to the skin of a patient afflicted with a dermatologic or other cosmetic or medical condition, or when administered by another route, results in an observable improvement in the patient's condition.

"Topical", when used to define a mode of administration, means that a material is administered by being applied to the skin.

"Topically effective" means that a material, when applied to the skin, produces a desired pharmacological result either locally at the place of application or systemically as a result of transdermal passage of an active ingredient in the material.

The Aromatic Aldehydes

The aromatic aldehydes include the compounds of Formula I as well as their acetal and hemiacetal equivalents shown in Formulas II and III.

Preferably, in the aromatic aldehyde compounds of Formula I above, $R^1$ is selected from the group consisting of a carbon-carbon single bond, methylene and ethylene. More preferably, $R^1$ is a carbon-carbon single bond.

Preferably, $R^2$ is selected from the group consisting of a carbon-oxygen single bond, methylene and ethylene. More preferably, $R^2$ is a carbon-oxygen single bond.

Preferably, $R^3$ is alkyl. More preferably, $R^3$ is methyl, ethyl or a propyl.

The four $R^4$s preferably include at least 2 hydrogens. More preferably, the remaining two $R^4$s are each independently, hydrogen, alkyl or alkoxy. Still more preferably, each of the four $R^4$s is hydrogen.

Preferably, each $R^5$ is independently alkyl, or in the case of the acetals of Formula II, the two $R^5$s together with the atoms to which they are attached form a heterocycloalkyl. More preferably each of the $R^5$s together with the atoms to which they are attached form 1,4-dioxacyclopentanyl or a substituted 1,4-dioxacyclopentanyl.

An especially preferred group of compounds of Formula I are those in which $R^1$ is a carbon-carbon single bond; $R^2$ is a carbon-oxygen single bond located in the 4 position on the aromatic ring relative to the aldehyde functionality, $R^3$ is methyl or ethyl and at least two $R^4$'s are each hydrogen.

In another of its composition aspects, this invention is directed to cosmetic and pharmaceutical compositions comprising a suitable carrier and containing one or more of the following aromatic aldehyde compounds:

2-methoxybenzaldehyde
2-ethoxybenzaldehyde
2-propoxybenzaldehyde
2-isopropoxybenzaldehyde
3-methoxyhenzaldehyde
3-ethoxybenzaldehyde
3-propoxybenzaldehyde
3-isopropoxybenzaldehyde
4-ethoxybenzaldehyde
4-propoxybenzaldehyde
4-isopropoxybenzaldehyde
2-methoxy-3-methylbenzaldehyde
2-ethoxy-3-methylbenzaldehyde
2-propoxy-3-methylbenzaldehyde
2-isopropoxy-3-methylbenzaldehyde
3-methoxy-4-methylbenzaldehyde
3-ethoxy-4-methylbenzaldehyde
3-propoxy-4-methylbenzaldehyde
3-isopropoxy-4-methylbenzaldehyde
2-butoxybenzaldehyde
4-butoxybenzaldehyde
4-pentyloxybenzaldehyde
4-hexyloxybenzaldehyde
4-heptyloxybenzaldehyde
3-ethoxy-4-methoxybenzaldehyde 4-ethoxy-3-methoxybenzaldehyde
3,4-diethoxybenzaldehyde
3-ethoxy-4-hexyloxybenzaldehyde
2-fluoro-4-methoxybenzaldehyde
2-fluoro-4-ethoxybenzaldehyde
2-fluoro-4-heptyloxybenzaldehyde
2-fluoro-4-octyloxybenzaldehyde
4-(methoxymethyl)benzaldehyde
4-(ethoxymethyl)benzaldehyde
3-(dodecyloxy)benzaldehyde
2,3-dimethoxybenzaldehyde
3,5-dimethoxybenzaldehyde
3-benzyloxy-4,5-dimethoxybenzaldehyde
4-benzyloxy-benzaldehyde
4-acetoxy-3,5-dimethoxybenzaldehyde
4-allyloxybenzaldehyde
3,4-dimethoxybenzaldehyde
2-carboxyl-3,4-dimethoxybenzaldehyde
2,4,5-trimethoxybenzaldehyde
3-chloro-4-methoxybenzaldehyde
3-butyloxy-4-methoxybenzaldehyde
3,5-dimethoxy-4-benzoxybenzaldehyde
2-acetoxy-3-methoxybenzaldehyde
3,5-dichloro-4-methoxybenzaldehyde
2-methyl-3,5-dimethoxybenzaldehyde
2,3,4,5-tetramethoxybenzaldehyde
2-formyl-3,6-dimethoxy-4,5-dimethylbenzaldehyde
2-acetyloxy-3-methoxy-6-bromobenzaldehyde
2-methoxy-6-(8-pentadecenyl)benzaldehyde
2-methoxy-5-acetylbenzaldehyde
2,5-dimethoxy-4-formylbenzaldehyde
4-octyloxybenzaldehyde
2-propoxy-5-carboxybenzaldehyde
2-butoxy-5-carboxybenzaldehyde
2-pentoxy-5-carboxybenzaldehyde
2-hexoxy-5-carboxybenzaldehyde
3-(4-methoxyphenoxy)benzaldehyde
3-(4-tertbutylphenoxy)benzaldehyde
as active ingredients Preferred aldehydes include: 2-ethoxybenzaldehyde, 2-acetoxy-3-methoxybenzaldehyde, 4-allyloxy-benzaldehyde, 4-ethoxybenzaldehyde, 4-propoxybenzaldehyde, 4-butoxybenzaldehyde, 4-pentyloxybenzaldehyde, and 4-hexyloxybenzaldehyde.

The aromatic aldehydes are generally employed as isolated compounds mixed with a suitable carrier.

2-methoxybenzaldehyde is among the aldehydes used herein. This is a synthetic flavoring substance approved by the Food and Drug Administration (FDA) for use in food for humans. The details for its use are discussed in Title 21 of the Code of Federal Regulations (CFR), chapter 1 part 172 subpart F Sec. 172.515.

General Synthetic Procedures

The aromatic aldehydes employed in the compositions and methods of this invention are either known compounds or are compounds that can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

For example, such compounds are readily prepared by acylation of the corresponding aryl compound with the appropriate acyl halide under Friedel-Crafts acylation reaction conditions. Additionally, the formyl compounds, i.e. those compounds where $R^4$ is hydrogen, can be prepared by formulation of the corresponding aryl compound using, for example, a disubstituted formamide, such as N-methyl-N-phenylformamide, and phosphorous oxychloride (the Vilsmeier-Haack reaction), or using $Zn(CN)_2$ followed by water (the Gatterman reaction). Numerous other methods are known in the art for preparing such aryl carbonyl compounds. Such methods are described, for example, in I. T. Harrison and S. Harrison, *Compendium of Organic Synthetic Methods*, Wiley, New York, 1971, and references cited therein.

Certain aromatic aldehyde compounds of Formula I can also be prepared by alkylation of the corresponding aryl hydroxy compound (e.g., 4-hydroxybenzaldehyde and the like). This reaction is typically conducted by contacting the aryl hydroxy compound with a suitable base, such as an alkali or alkaline earth metal hydroxide, fluoride or carbonate, in a inert solvent, such as ethanol, DMF and the like, to deprotonate the hydroxyl group. This reaction is generally conducted at about 0° C. to about 50° C. for about 0.25 to 2 hours. The resulting intermediate is then reacted in situ with about 1.0 to about 2.0 equivalents of an alkyl halide, preferably an alkyl bromide or iodide, at a temperature of from about 25° C. to about 100° C. for about 0.25 to about 3 days.

Additionally, various aromatic aldehydes of Formula I can be prepared by reduction of the corresponding aryl nitriles. This reaction is typically conducted by contacting the aryl nitrile with about 1.0 to 1.5 equivalents of a hydride reducing agent, such as $LiAlH(OEt)_3$, in an inert solvent such as diethyl ether, at a temperature ranging from about −78° to about 25° C. for about 1 to 6 hours. Standard work-up conditions using aqueous acid then provides the corresponding aryl aldehyde.

The aromatic aldehydes of Formula II and III employed in the compositions and methods are either known compounds or compounds that can be prepared from known compounds by conventional procedures. The hemiacetals can be formed by either acid or base catalyzed reaction of the corresponding aldehyde with and alcohol. If a single equivalent of the alcohol is added to the carbonyl, the hemiacetal is formed. Addition of 2 equivalents of an alcohol to the carbonyl produces the acetal. Acetal formation is acid catalyzed and is typically conducted by adding 1 mol of aldehyde and a 0.1 mol of $CaCl_2$ to 1.9 mol of ethanol. The reaction mixture is held at room temperature for 1 to 2 days. Standard work up conditions provide the acetal protected aromatic aldehyde.

Pharmaceutical and Cosmetic Compositions and Their Use

The aromatic aldehydes are administered in the form of a pharmaceutical or cosmetic composition. Such compositions can be prepared in manners well known in the pharmaceutical and cosmetic arts and comprise at least one active compound.

Generally, the compositions of this invention are administered in a cosmetic amount or in a therapeutically effective dose. The amount of the compound actually administered in therapeutic settings may typically be determined by a physician, in the light of the relevant circumstances, including the condition to be treated, the chosen route of administration, the actual compound administered, the age, weight, and response of the individual patient, the severity of the patient's symptoms, and the like. In cosmetic settings the amount to be applied is selected to achieve a desired cosmetic effect.

The cosmetic compositions of this invention are to be administered topically. The pharmaceutical compositions of this invention are to be administered topically, transdermally or systemically such as orally or by injection.

In such compositions, the aromatic aldehyde compound is usually a minor component (from about 0.001 to about 20% by weight or preferably from about 0.01 to about 10% by weight) with the remainder being various vehicles or carriers and processing aids helpful for forming the desired dosing form.

Topical cosmetic forms and topical pharmaceutical dosing forms can include lotions, shampoos, soaks, gels, creams, ointments and pastes. Lotions commonly employ a water or alcohol base. Gels are semi-solid emulsions or suspensions. Creams generally contain a significant proportion of water in their base while ointments and creams are commonly more oily.

Liquid forms, such as lotions suitable for topical administration or for cosmetic application, may include a suitable aqueous or nonaqueous vehicle with buffers, suspending and dispensing agents, thickeners, penetration enhancers, and the like. Solid forms such as creams or pastes or the like may include, for example, any of the following ingredients, water, oil, alcohol or grease as a substrate with surfactant, polymers such as polyethylene glycol, thickeners, solids and the like. Liquid or solid formulations may include enhanced delivery technologies such as liposomes, microsomes, microsponges and the like.

The above-described components for liquid, semisolid and solid topical compositions are merely representative. Other materials as well as processing techniques and the like are set forth in Part 8 of *Remington's Pharmaceutical Sciences,* 17th edition, 1985, Mack Publishing Company, Easton, Pa., which is incorporated herein by reference.

When pharmaceutical compositions are to be administered transdermally they typically are employed as liquid solutions or as gels. In these settings the concentration of active aldehyde ranges from about 0.1% to about 20%, and preferably from about 0.1% to about 5%, of the composition with the remainder being aqueous mixed or nonaqueous vehicle, such as alcohols and the like, suspending agents, gelling agents, surfactant, and the like. Examples of suitable such materials are described below.

The aldehyde-containing compositions of this invention can also be administered in sustained release transdermal forms or from transdermal sustained release drug delivery systems. A description of representative sustained release materials can be found in the incorporated materials in *Remington's Pharmaceutical Sciences.*

The compositions for systemic administration include compositions for oral administration, that is liquids and solids, and compositions for injection.

Compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical occupant. Typical unit dosage forms include profiled, premeasured ampules or syringes of the liquid compositions or pills, tablets, capsules or the like in the case of solid compositions. In such compositions, the aromatic aldehyde is usually a minor component (from about 0.01 to about 20% by weight or preferably from about 0.1 to about 15% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an occupant such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the aromatic aldehyde in such compositions is typically a minor component, often being from about 0.005 to 5% by weight with the remainder being the injectable carrier and the like.

The above-described components for orally administrable or injectable compositions are merely representative. Other materials as well as processing techniques and the like are set forth in the part of *Remington's Pharmaceutical Sciences* noted above.

The following formulation examples illustrate representative cosmetic and pharmaceutical compositions of this invention. The present invention, however, is not limited to the following pharmaceutical compositions.

Formulation 1—Liquid

A compound of Formula I (125 mg), and xanthan gum (4 mg) are blended, passed through a No. 10 mesh U.S. sieve, and then mixed with a previously made solution of microcrystalline cellulose and sodium carboxymethyl cellulose (11:89, 50 mg) in a water/isopropanol (75:25) mixture. Sufficient water/isopropanol are then added to produce a total volume of 5 mL.

Formulation 2—Cream

A commercial mineral oil-water cold cream base is obtained. To 100 grams of this base, 0.75 grams of a compound of Formula I as a fine powder or liquid is added with continuous mixing and stirring to suspend the powder in the base and yield a cosmetic or pharmaceutical composition.

This composition includes the following: deionized water (57.6% by weight); niacinamide (2.0%); glycerin (4.0%); phenonip (1.0%); propylene glycol (5.0%); transcutol (3.2%); jojoba Oil (3.5%); isocetyl alcohol (2.0%); isocetyl stearate (3.5%); mineral oil (3.0%); 4-ethoxybenzaldehyde (1.0%); isostearyl palmitate (3.0%); PEG-7 glyceryl cocoate (2.0%); Glycereth-7 (2.0%); POLYSORBATE-20™ (0.2%); cetyl ricinoleate (1.0%); glyceryl stearate/PEG-100 stearate (4.0%); and SEPIGEL™ (2.0%).

Formulation 3—Tablets

A compound of Formula I is mixed with dry gelatin binder and starch diluent in a 0.1:1:1 weight ratio. A lubricating amount of magnesium stearate is added and the mixture is tabletted into 210 mg tablets containing 10 mg of active aromatic aldehyde.

Formulation 4—Injection

A compound of Formula I is dissolved in injectable aqueous saline medium at a concentration of 1 mg/ml.
Utility and Dosing The composition and methods of this invention can be used topically to treat dermatological conditions such as
   actinic keratosis, acne,
allergic contact dermatitis,
atopic eczema,
contact dermatitis,
eczema,
erythema,
hand eczema,
itch,
irritant contact dermatitis,
psoriasis,
seborrhoric eczema,
rosacea,
alopecia areata,
damage from radiation, including UV radiation, IR radiation and any other ionizing radiation,
and the like.

The compositions, both cosmetic and pharmaceutical, can also be used to treat and prevent sunburn and to treat and prevent other forms of UV-induced inflammation and damage, and damage from other forms of ionizing radiation.

In these applications the cosmetic and pharmaceutical compositions are administered topically to achieve a desired cosmetic effect or a topical therapeutic effect.

In these uses the dose levels or application levels can be expressed in terms of the amount of active aromatic aldehyde delivered to the skin. For example, 1 to about 5 doses or applications per day, each containing from about 0.001 g to about 1 gram of active aldehyde can be used.

Alternatively, dose levels can be expressed in terms of the volume of formulated composition administered. For example, 1 to about 5 doses or applications per day, each containing from about 1 to about 30 grams of composition containing from about 0.01% to about 10% by weight of active aldehyde and especially from 0.02% to about 8% by weight.

When used in a sun care product, such as sun-care lotion, the concentration of aldehyde can be as set forth above and the product can be applied as needed based on the intensity and duration of sun exposure.

Additionally, since the aromatic aldehydes have been discovered to effectively inhibit the release of cytokines, such a IL-1α, such compounds are useful for treating diseases characterized by an overproduction or a dysregulated production of cytokines, particularly IL-1α. Elevated levels of IL-1 and other cytokines are associated with a wide variety of inflammatory conditions, including rheumatoid arthritis, septic shock, erythema nodosum leprosy, septicemia, adult respiratory distress syndrome (ARDS), inflammatory bowel disease (IBD), uveitis, damage from ionizing radiation and the like.

The relationships between these cytokines and related materials and the inflammatory processes are described in more detail below at "Biology and Testing".

In the case of transdermal administration to treat such inflammatory conditions, one can administer a quantity of composition to a surface area of skin suitable to achieve an active aldehyde concentration in the systemic bloodstream of from about 0.5 to about 1000 micromolar and especially from about 1 to about 500 micromolar.

Injection dose levels for treating inflammatory conditions range from about 0.01 mg/kg/hour to at least 1 mg/kg/hour, all for from about 1 to about 120 hours and especially 24 to 96 hours. A preloading bolus of from about 0.01 mg/kg to about 1 mg/kg or more may also be administered to achieve adequate steady state levels.

With oral dosing, one to five and especially two to four and typically three oral doses per day are representative regimens. Using these dosing patterns, each dose provides from about 0.01 to about 10 mg/kg of the aromatic aldehyde, with preferred doses each providing from about 0.01 to about 5 mg/kg.

The aromatic aldehydes can be administered as the sole active agent or they can be administered in combination with other agents.

Biology and Testing

The examples include a number of in vitro studies to investigate the ability of these aldehydes to block various inflammatory processes in the skin. For these studies primary human keratinocytes and dermal fibroblast cell strains have been used as well as THP-1 monocytes and the Jurkat T-cell derived cell line. The in vitro experiments used to assess the anti-inflammatory activities of the aldehydes were selected on the basis of current knowledge about the skin inflammatory process. FIG. 1 depicts the events involved in cutaneous inflammation.

Inflammation in the skin is characterized by itching, pain, redness, swelling and, frequently, rough and flaky skin. These symptoms result from changes in blood flow to the site of inflammation, increased vascular permeability, the migration of cells from the circulation into the tissue, and the release of soluble mediators including cytokines, prostaglandins and chemokines. Skin inflammation can be triggered by: 1) infection caused by bacteria, parasites, fungi, or viruses, 2) injury resulting from physical trauma including burns, UV and ionizing radiation, 3) contact with chemical irritants, and 4) exposure to a foreign body such as an allergen which triggers an immune response.

Inflammation can be characterized as acute or chronic. Acute skin inflammation can result from exposure to UV radiation (UVR), ionizing radiation or contact with chemical irritants and allergens. In contrast, chronic inflammation results from a sustained immune cell mediated inflammatory response. Acute inflammatory responses are typically resolved within 1 to 2 weeks with little accompanying tissue destruction. Chronic inflammatory responses, however, are long-lasting because the antigen that triggered the response persists in the skin. This leads to continued recruitment of immune cells into the tissue, particularly T lymphocytes, which then produce and secrete high levels of many inflammatory mediators. Chronic inflammation leads to significant and serious tissue destruction.

Figure 2:
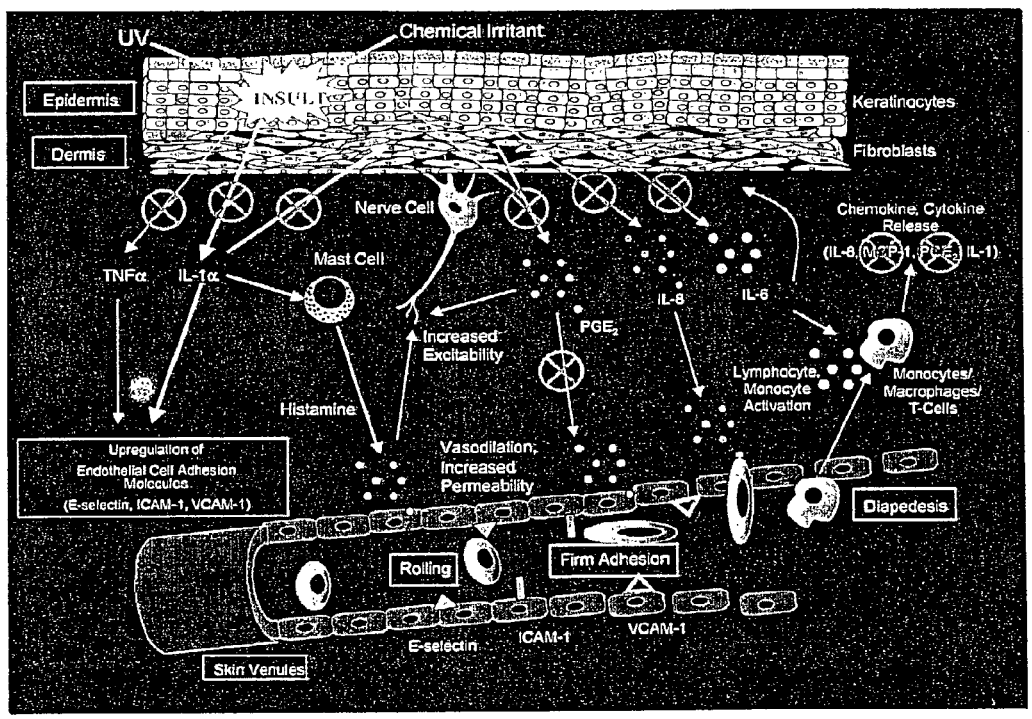
FIG. 2: A repeat of FIG. 1 illustrating those inflammatory processes which are effectively treated using the present invention.

Regardless of the stimulus that triggers either an acute or chronic cutaneous inflammatory response, the initial events are similar and are shown in FIGS. 1 and 2. Triggering stimuli, such as UV radiation, induce keratinocytes in the skin to produce various cytokines including the key inflammatory cytokine, Interleukin-1 (IL-1). These cells also produce Tumor Necrosis Factor (TNF-α) and prostaglandin E2 (PGE-2). PGE-2 causes vasodilation of blood vessels near the site of injury and also increases the sensitivity of sensory nerve endings resulting in the sensation of itching and pain. The principal action of TNF-α is to increase the production of adhesion molecules on the surface of endothelial cells lining the blood vessels. These adhesion molecules act as anchors within the blood vessel allowing immune cells moving through the circulation to attach to the endothelium, an event that can lead to the diapedsis (movement) of these cells from the circulation and into the tissue. IL-1 produced by keratinocytes binds to specific receptors on fibroblasts within the dermis and activates signaling pathways that lead to the induction of many pro-inflammatory genes, such as those for COX-2, IL-8 and IL-6. IL-1 also binds to specific receptors on mast cells resulting in the production and secretion of histamine (which also increases nerve ending sensitivity), cytokines and other inflammatory mediators. In addition to responding to keratinocyte-derived IL-1, fibroblasts can also be directly activated by the triggering stimulus (e.g. UVR) and this further stimulates the expression of pro-inflammatory genes resulting in the production of PGE-2, the chemokine IL-8, as well as collagenase-1 (MMP-1). IL-8 stimulates diapedsis (chemotaxis, movement) of neutrophils, monocytes and ultimately lymphocytes from the endothelial cells where they have attached as a result of the TNF-α induced increase in adhesion molecules. Once in the tissue, neutrophils and monocytes produce additional cytokines (IL-1, IL-12), and chemokines including monocyte chemotactic protein (MCP-1), a potent chemokine that accelerates the movement of monocytes into the tissue and helps transform them into macrophages. Mature macrophages in turn produce a variety of matrix metalloproteinases (MMPs) that degrade extracellular matrix proteins and thus reduce the strength, elasticity and thickness of the skin.

If the inflammatory response is maintained by the continued presence of an antigen in the skin as is the case with chronic and destructive cutaneous diseases such as psoriasis and atopic dermatitis, the persistence of the antigen causes T-lymphocytes to enter the tissue site and become activated. This activation leads to the production of cytokines such as TNF-α, monocyte chemotactic protein-1 (MCP-1), IL-8, IL-12, and interferon-γ (INF-γ). Released IL-12 causes the T-lymphocytes to proliferate rapidly and to produce a wide range of cytokines, growth factors and other inflammatory mediators. These released products further activate macrophages, recruit monocytes, increase tissue destruction and cause accelerated and uncontrolled growth of skin cells, particularly keratinocytes. The result is pronounced skin inflammation with redness, pain, itching and scaling of the skin as the keratinocytes move rapidly to the surface and "flake off". Further, the rapid shedding of keratinocytes at the surface compromises the barrier function of the stratum corneum resulting in water loss and dry skin.

A common finding in inflammation is that cells in the skin respond to inflammatory stimuli by activating either one of two intracellular signaling pathways (or in some cases both pathways). These pathways are commonly referred to as the Stress Activated Kinase (SAK) pathway and the NF-kB pathway. The SAK pathway leads to the activation of the AP-1 transcription factor, which then binds to and activates several inflammatory genes including COX-2, IL-6 and MCP-1. Activation of the NF-kB pathway results in NF-kB protein translocation to the nucleus and activation of NF-kB driven inflammatory genes such as IL-8, MMP-1, TNF-α and the adhesion molecule, VCAM-1. Interestingly, many inflammatory genes including IL-1 have promoter elements that bind both AP-1 and NF-kB transcription factors and are thus regulated to some extent by both signaling pathways. The Cutanix screening assays are designed to determine which pathway is blocked by the compound under investigation, or if both pathways are effectively inhibited. A compound with the capacity to block the transcription of inflammatory genes regulated by each of these pathways will likely provide significant anti-inflammatory effects when applied topically. For each putative anti-inflammatory compound under consideration the initial screening program concentrates on the following target sites for intervention:

1. Inhibiting the production of IL-1 and PGE-2 in UVR or tetradecanoly phorbol acetate (TPA)-treated keratinocytes.

2. Inhibiting the production of PGE-2 in UVR-treated dermal fibroblasts.

3. Inhibiting the induction of PGE-2 in IL-1 treated fibroblasts.

Because one of the most common activators of skin inflammation is sunlight, specifically UVB radiation, the determination of a compound's ability to block the induction of pro-inflammatory PGE-2 by UVR in both keratinocytes and fibroblasts represents a logical first step in the screening process. In addition, because skin inflammation is often triggered by contact with chemical irritants or allergens, the use of TPA, which is known to trigger an inflammatory response in the skin, provides an additional model for the analysis of anti-inflammatory activities of test compounds. Finally, because IL-1 is one of the most important mediators and propagators of inflammation and is rapidly induced by an inflammatory stimulus, such as UVR, determining the ability of a potential anti-inflammatory compound to block either the production or action of IL-1 is a critically important initial screening study. As shown in FIGS. 1 and 2, by blocking IL-1 production from keratinocytes, not only is the activation of fibroblasts suppressed but the activation of mast cells is also blocked thus preventing the release of histamine and other inflammatory mediators. Furthermore, inhibition of IL-1 production in the skin would prevent the activation of a large number of inflammatory genes that are stimulated solely by IL-1. These include COX-2, MMP-1, and a variety of cytokine and chemokine genes.

For all of the initial screening studies described herein, cells in culture are exposed to the appropriate agonist, (i.e. UVR, TPA or IL-1) and then incubated in medium for 24 or 48 hours in the presence or absence of the compound under investigation. At 24 and 48-hour time points, medium from the cells is removed and assayed for a number of inflammatory mediators by ELISA.

Only primary keratinocyte and fibroblast cell strains were used, not immortalized cell lines, for the screening studies. The use of normal cells from the skin increases the probability that results from in vitro studies will be predictive of effects of a given compound when applied topically.

Aldehydes that are found to completely (100%) suppress PGE-2 induction at a concentration of 100 micromolar or less are then subjected to more demanding dose-response studies including the following sequence of experiments:

1. Assessment by ELISA of a compound's ability to block a variety of UVR, TPA, or IL-1 induced inflammatory mediators in keratinocytes and fibroblasts including IL-6, TNF-α, IL-8, and MMP-1.

2. Assessment by ELISA of a compound's ability to block the production and secretion of inflammatory mediators by monocytes (THP-1 monocyte line) stimulated by lipopolysaccharide (LPS) and by T lymphocytes (Jurkat cells) stimulated with an antibody ligand that activates the cells.

3. The use of RPA (ribonuclease protection analysis) to determine if a compound is acting at the gene level to suppress the activity of specific inflammatory genes stimulated by exposure of cells to various agonists including UVR, IL-1, TPA, or LPS (lipopolysaccharide). Cutanix has developed a customized RPA "cocktail" for keratinocytes, fibroblasts, T-cells, and monocytes to simultaneously measure the expression of cell-type specific inflammatory genes in cells stimulated with UVR, IL-1, TPA or LPS in the presence or absence of the compound under investigation.

4. The use of microarray gene analysis to simultaneously examine the effect of any compound on the expression of more than 5,500 genes specific for cells present in the skin. The gene arrays used were purchased from Research Genetics and provide read-outs on genes known to be expressed in the skin.

The aldehydes can suppress a number of pro-inflammatory mediators and FIG. 2 identifies some of the events that are likely inhibited by the aldehydes in vivo (shown by the circled X).

EXAMPLES

The following examples are provided to further describe the invention and are not intended as limitations on the scope of the invention which is defined by the appended claims.

Example 1

An initial in vitro experiment was conducted to demonstrate the activity of the aromatic aldehyde, 4-ethoxybenzaldehyde, ("4-EB") as a topically administered pharmaceutical.

For this experiment, human skin fibroblasts were seeded into 12 well culture dishes at a density of 80,000 cells/well in tissue culture medium and left overnight to attach to the dish. The next day, medium was removed and replaced with fresh medium containing either 1% ethanol as a diluent control, IL-1 at a concentration of 500 picograms/ml, or IL-1 plus 4-EB at either 250 µM or 500 µM. Cells were incubated for an additional 24 hours and at this time, the medium was removed and assayed by ELISA for the presence of PGE-2 in the culture medium. The results show that IL-1 caused a 17.8 fold increase in PGE-2 (control=727 pg/$10^6$ cells: IL-1=12,976 pg/$10^6$ cells). However, cells treated with either concentration of 4-EB showed a complete inhibition of the IL-1 induction of PGE-2.

Example 2

Figure 3:
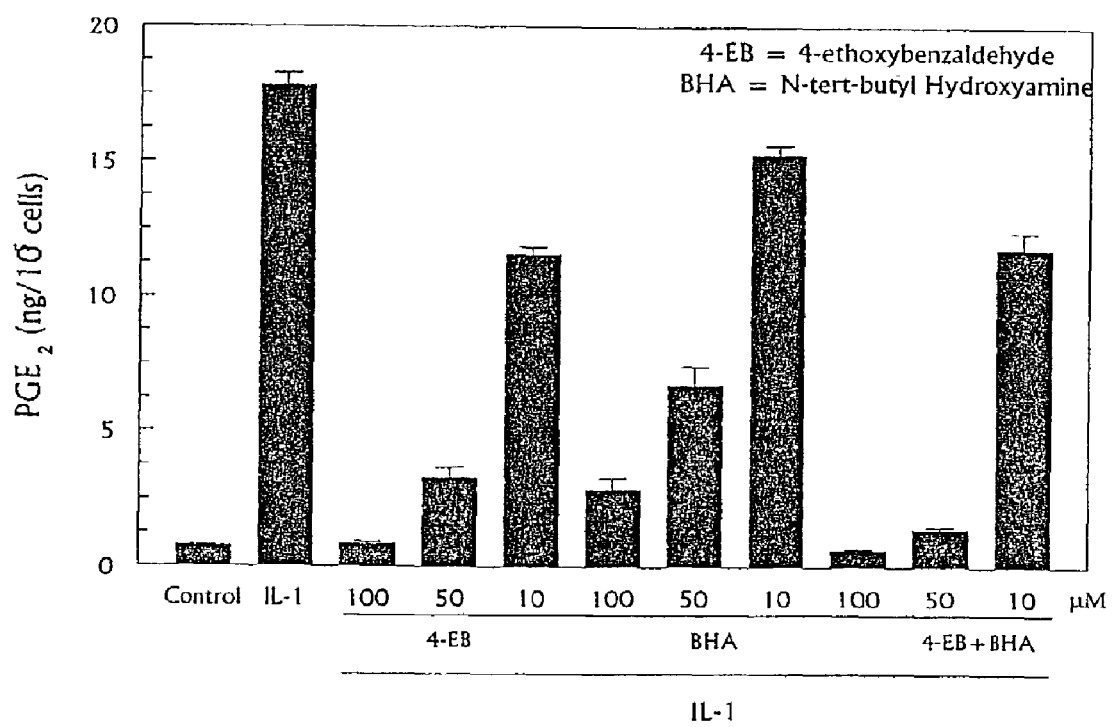

Subsequent studies were carried out to determine the dose-response of human skin fibroblasts to 4-EB. 4-EB completely blocked the IL-1 induction of PGE-2 at 100 µM, blocked 82% of the PGE-2 induction at 50 µM, and blocked 35% at a concentration as low as 10 µM. The results of the study are provided graphically in FIG. 3.

Example 3

Subsequent in vitro experiments were conducted to demonstrate the activity of other aromatic aldehydes compared to the 4-ethoxybenzaldehyde, ("4-EB") as a topically administered pharmaceuticals. The compounds tested were 2-ethoxy-benzaldehyde (2-EB), 3-ethoxybenzaldehyde (3-EB), and 4-methoxy-benzaldehyde (4MB).

For this experiment, human skin fibroblasts were seeded into 12 well culture dishes at a density of 80,000 cells/well in tissue culture medium and left overnight to attach to the dish. The next day, medium was removed and replaced with fresh medium containing either 1% ethanol as a diluent control, IL-1 at a concentration of 500 picograms/ml, or IL-1 plus one of the compounds under investigation at a concentration of 1, 10, 50 or 100 µM. Cells were incubated for an additional 24 hours and at this time, the medium was removed and assayed by ELISA for the presence of PGE-2 in the culture medium. The results show that IL-1 caused a 4 to 22 fold increase in PGE-2.

Percent inhibitions as shown in the detailed results of FIG. 4A) are as follows: 2-EB, 82.9% and 58.9% at 100 µM and 50 µM; 3-EB, 41.2% and 42.6% at 100 µM and 50 µM; 4-EB, 81.5% at 100 µM.

Concentrations of 10 or 50 µM 4MB did not appear to inhibit the IL-1 induced production of PGE-2 in the fibroblasts. Percent inhibitions as shown in the detailed results of FIG. 4B) are as follows: 4-MB, 13.6% and 16.2% at 50 µM and 10 µM.

Example 4

Similar in vitro studies as those described in Example 3 were run using human skin keratinocytes. The experimental set up was the same as described for Example 3 but replacing IL-1 with tetradecanoyl phorbol acetate (TPA) at a concentration of 32 nM as the agonist. The compounds tested were 2-ethoxy-benzaldehyde (2-EB), and 3-ethoxybenzaldehyde (3-EB) and 4-ethoxybenzaldehyde (4-EB) in concentrations of either 10, 50, or 100 µM. The results show that TPA caused a 3.5 fold increase in PGE-2. However, treatment with any of these compounds blocked PGE-2 production by at least 50%.

Figure 5:
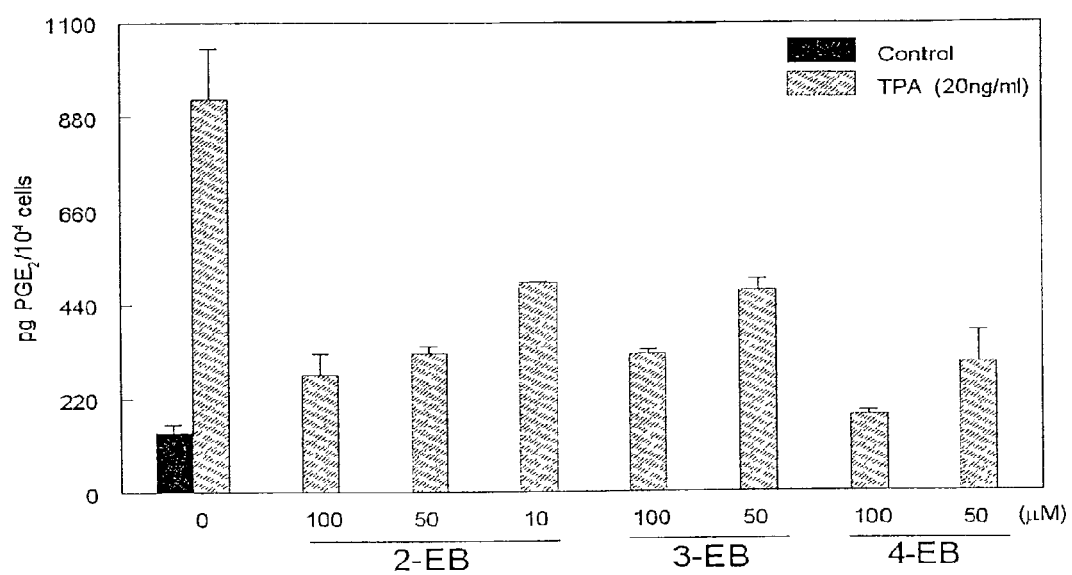
FIG. 5: A bar graph which shows the effects of aldehydes employed in the compositions of this invention on tetradecanoyl phorbol acetate "TPA"-induced $PGE_2$ expression in keratinocytes.
Figure 8A:
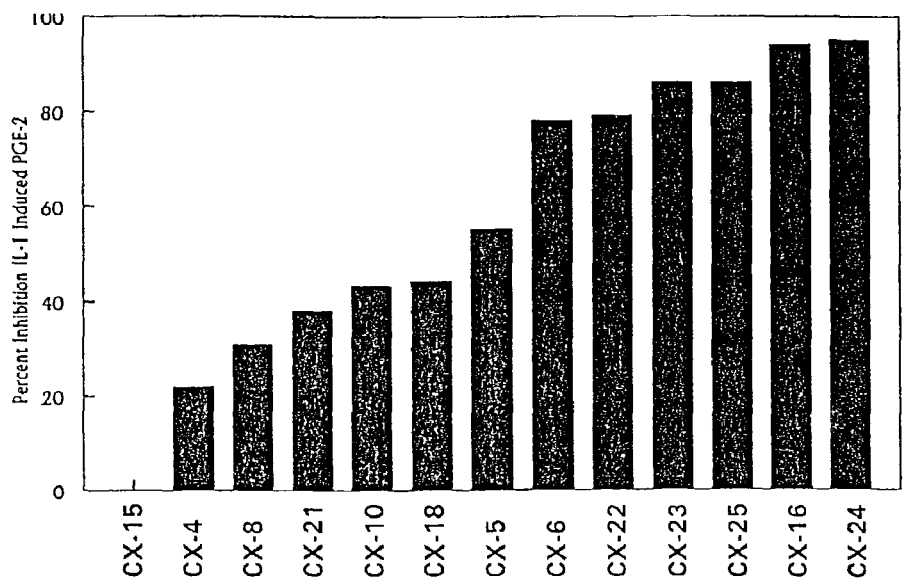
Figure 8B:
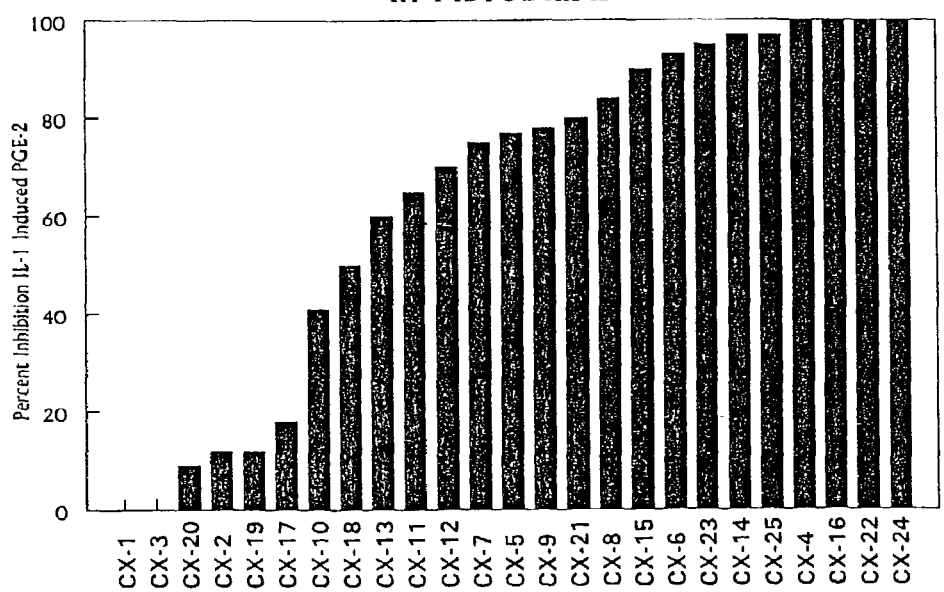
Figure 9A:
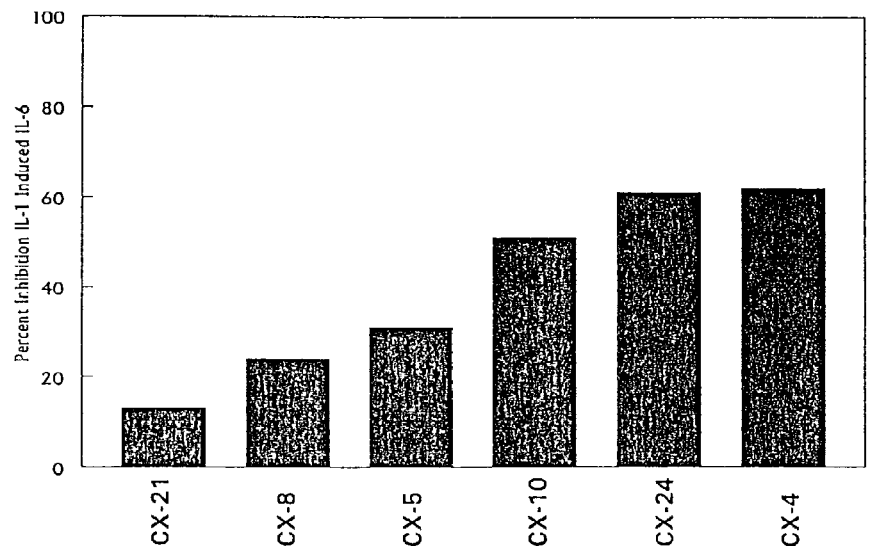
Figure 9B:
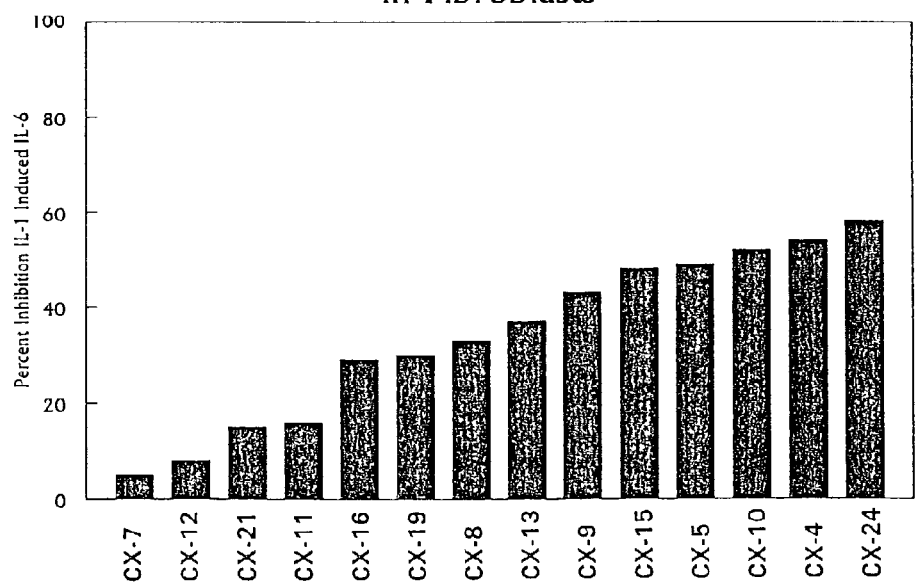
Figure 10A:
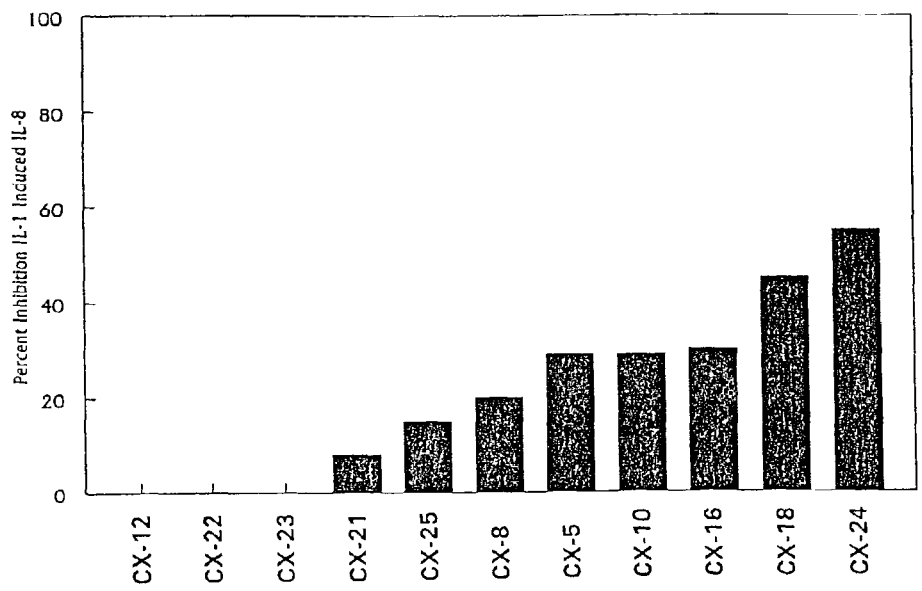
Figure 10B:
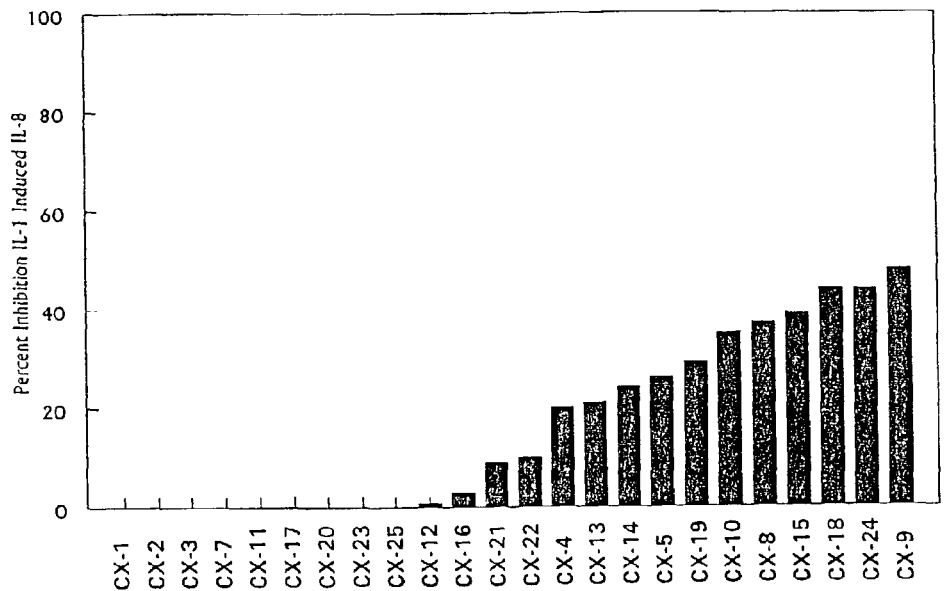

The percent inhibitions as shown in the detailed results in FIG. 5 are as follows: 2-EB, 83%, 76.6%, and 55.2% inhibition at 100 µM, 50 µM, and 10 µM; 3-EB, 76.7% and 57.7% at 100 µM and 50 µM; 4-EB, 94.9% and 79.9% at 100 µM and 50 µM.

Example 5

In vitro experiments were conducted to demonstrate the activity of a series of aromatic aldehydes as a topically administered pharmaceuticals. The compounds tested and the measured results are tabulated in FIG. 6, and shown graphically in FIGS. 8-11. These data include results for aldehydes of Formula I and also include results for other related compounds.

For this experiment, human skin fibroblasts were seeded into 12 well culture dishes at a density of 80,000 cells/well in tissue culture medium and left overnight to attach to the dish. The medium was then replaced with PBS for a challenge with either UV-light or with IL-1. After irradiation or introduction of IL-1, the PBS was removed and culture medium containing the appropriate compound (or DMSO for controls) was then added and the cells cultured for an additional 24 hours. At that time, the medium was removed and assayed by ELISA for the presence of PGE-2, IL-1, IL-6, IL-8, or MMP-1 in the culture medium. The levels of protein in the conditioned medium were measured and reported as percent inhibition relative to diluent controls.

IL-1 Challenge

On the second day, the medium was removed and replaced with fresh medium containing either 1% ethanol as a diluent control, IL-1 at a concentration of 500 picograms/ml, or IL-1 plus one of the compounds under investigation at a concentration of 100, 10, or 1 µM.

UV-light Challenge

On the second day, the medium was removed and replaced with fresh PBS for irradiation. The fibroblasts were then irradiated with 50 mJ of UVB. UVB irradiation was obtained by illuminating the samples with an FS-20 sunlamp through the lids of the multi-well plates in order to filter out the UVC radiation. After irradiation the PBS solution was removed and replaced with a solution containing either 1% ethanol as a diluent control, or one of the aldehyde compounds at a concentration of 100, 10, or 1 µM. The cells were incubated for another 24 hours and the medium was then removed for the ELISA assays and the cells were counted.

Example 6

Similar in vitro studies as those described in Example 5 were run using human skin keratinocytes. The experimental set up was the same as described for Example 5. The products assayed by ELISA for the presence of PGE-2, IL-1, IL-6, IL-8, MMP-1, or TNF-α in the culture medium.

For the cells challenged by a biochemical agonist, IL-1 was replaced with tetradecanoyl phorbol acetate (TPA) at a concentration of 32 nM. When UV-light was used to challenge the cells, they were exposed to 75 mj of UVB, obtained by illuminating the samples with an FS-20 sunlamp through the lids of the multi-well plates in order to filter out the UVC radiation.

The compounds tested were in concentrations of either 100, 10, or 1 µM, and the protein expression levels are reported in percent inhibition of growth.

Figure 12A:
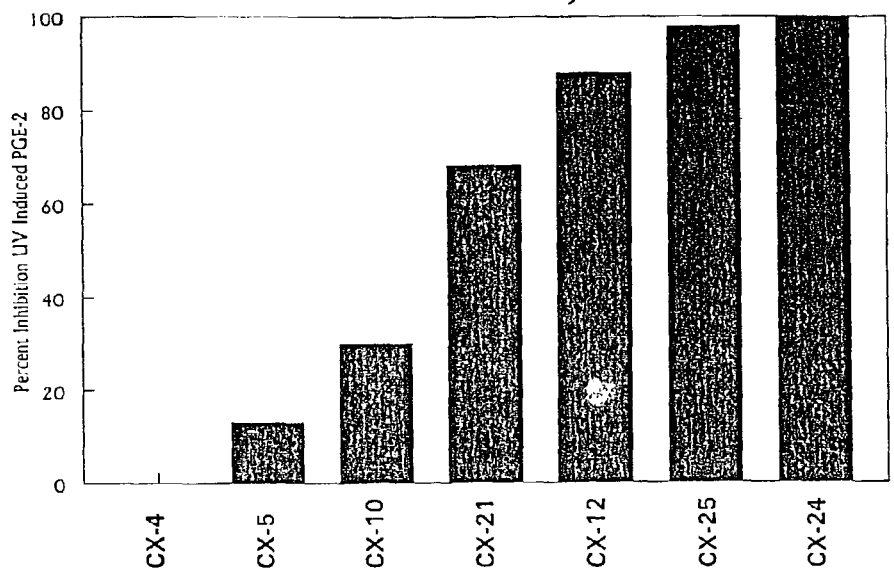
Figure 12B:
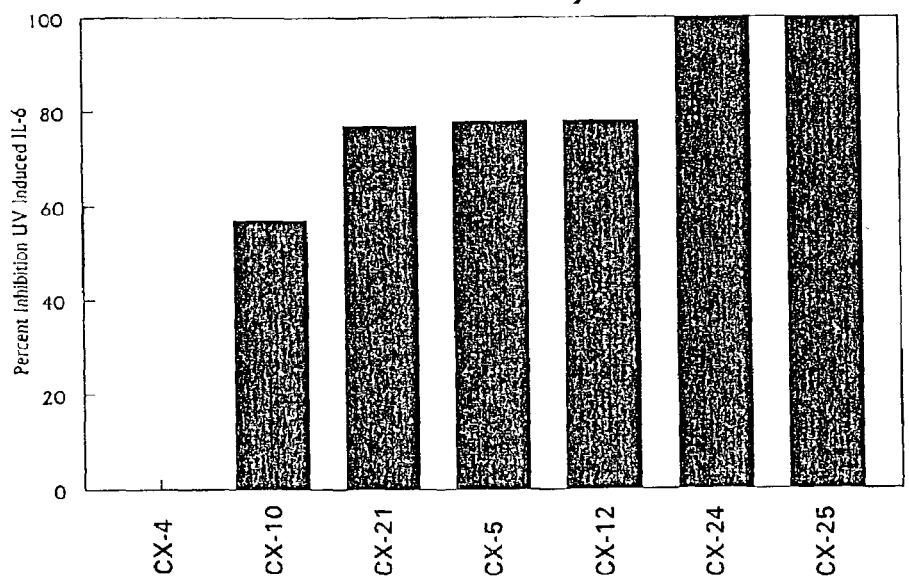
Figure 14A:
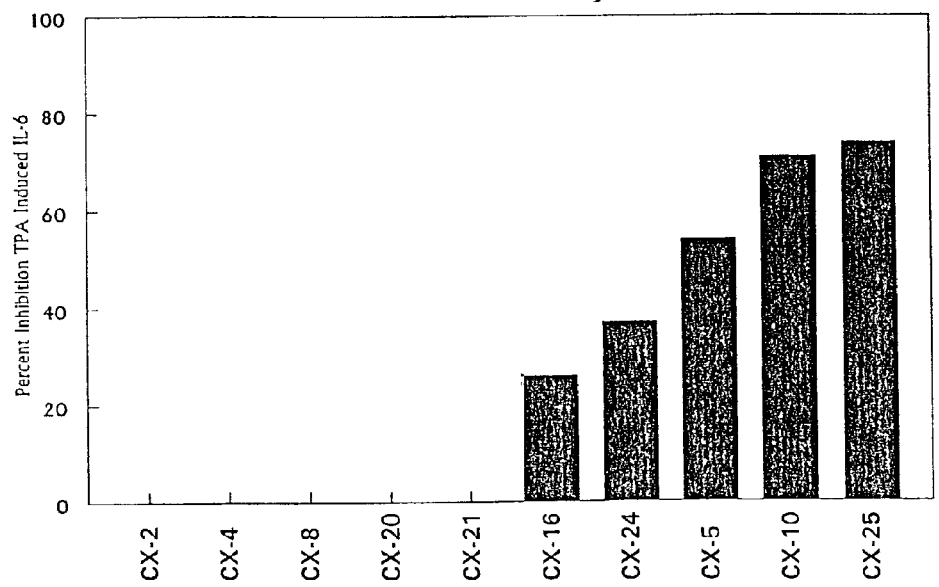
Figure 14B:
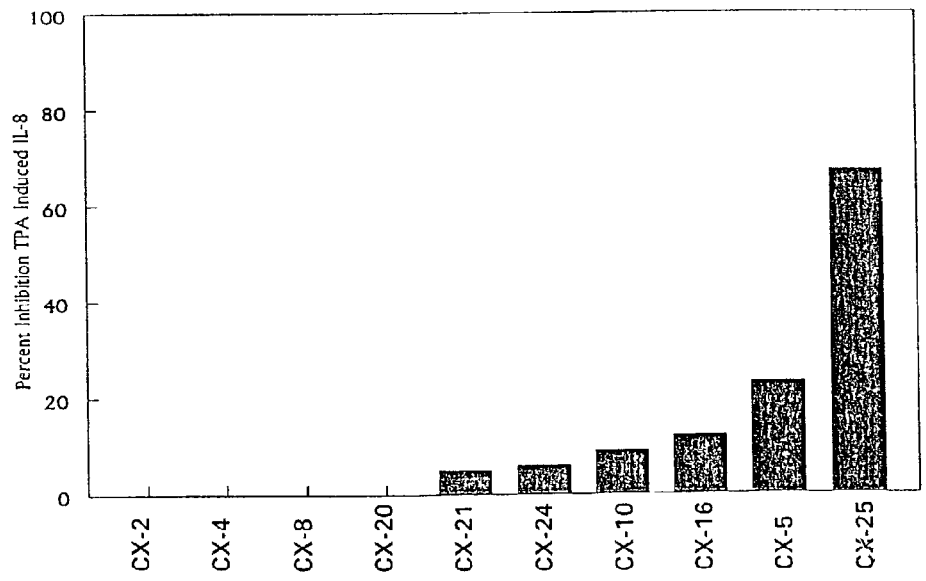

The measured percent inhibitions are tabulated in FIG. 7 and shown graphically in FIGS. 12-14.

Example 7

Because of the marked anti-inflammatory effects seen when 4-EB was used in human fibroblast cell culture models, in vivo studies were carried out to determine if topically applied 4-EB could block an inflammatory response in humans. While the details provided herein are for a specific compound, the same tests can be used on any of the aromatic aldehydes of the present invention.

A topical lotion was developed for 4-EB which consists of the following:

| Aqueous Phase | |
|---|---|
| Deionized water | 57.6% (by weight) |
| Niacinamide | 2.0% |
| Glycerin | 4.0% |
| Phenonip | 1.0% |
| Oil Phase | |
| Propylene glycol | 5.0% |
| Transcutol | 3.2% |
| Jojoba Oil | 3.5% |
| Isocetyl alcohol | 2.0% |
| Isocetyl Stearate | 3.5% |
| Mineral Oil | 3.0% |
| 4-ethoxybenzaldehyde | 1.0% |
| Isostearyl Palmitate | 3.0% |
| PEG-7 Glyceryl Cocoate | 2.0% |
| Glycereth-7 | 2.0% |
| Polysorbate-20 ™ | 0.2% |
| Cetyl Ricinoleate | 1.0% |
| Glyceryl Stearate/ PEG-100 Stearate | 4.0% |
| Thickener | |
| Sepigel ™ | 2.0% |

This lotion was then tested by Franz cell percutaneous absorption analysis to determine how much 4-EB could penetrate human skin over a 24 hour period. The lotion formulation above provided a flux rate of 4-EB through human skin of 30-50 micrograms/hour.

This lotion was then tested to determine if it could prevent an inflammatory response when applied topically to human skin. For this study a lab volunteer was irradiated on a quarter sized spot on the inner forearm with 60-80 mJ of UVB light (a sunlamp). This dose was sufficient to cause a highly visible red erythema response Immediately following irradiation on both arms, one arm was treated with the above 4-EB lotion while the other arm was treated with the same lotion formulation but with no 4-EB. Within 2-6 hours after irradiation the vehicle-treated arm developed a pronounced red erythema response at the site of irradiation while the 4-EB lotion treated spot did not. Even the next day, 14 hours post-irradiation, the spot treated with 4-EB showed no redness. This study demonstrates that topically applied 4-EB has marked anti-inflammatory activity.

In addition to its anti-inflammatory activity compounds of the present invention, either alone or in combination with other compounds, such as ethyl vanillin, may have anti-aging properties. One of the classical symptoms of skin aging is an increase in collagenase activity in dermal fibroblasts which destroys collagen thereby leading to sagging skin and wrinkles.

Implications of the Results in Terms of Potential Uses of the Discovery

Anti-aging

The finding that aromatic aldehydes of the present invention inhibit the activity of inflammatory genes in cultured skin cells and that they can block an inflammatory response in vivo when applied topically suggests wide utility for these compounds in the cosmetic, dermatology and oral drug markets. In the cosmetic market, these compounds when formulated for topical use can be expected to lower chronic sun-induced inflammation, which causes the activation of genes in skin cells that destroy the skin matrix. By inhibiting sun-induced genes such as MMP-1 (collagenase), gelatinase, and cytokines IL-1, IL-12, etc. 2-EB, 3-EB and 4-EB will prevent the further breakdown of the skin and thus lessen the production of lines and wrinkles, sagging skin, and thinning of skin. It is likely that these aromatic aldehydes will stimulate genes that support the skin matrix such as collagen (studies ongoing). Thus, this product can be used as a "skin restorative" product for sun-damaged skin It has its utility in treating actinic keratoses by both preventing their formation and actually reducing the size and number of existing keratoses.

Sun Care Products

The finding that topically applied 4-EB, or any other compound of this invention, can completely prevent the onset of a sunburn by UVB exposure suggests the use of aromatic aldehydes in sun care products including pre-sun, sun-tan lotions, and after-sun products. It is not suggested that the molecules have sun-screen properties (which they probably do to some extent) but that they can actually arrest the progression of a sunburn AFTER the skin has already been exposed to the UV rays of the sun. Although it has been shown that topical application of the product immediately after UVB exposure will prevent the onset of sunburn, it is also possible that application of the product even after the sunburn has appeared may: 1) prevent the continued progression of sunburn, and 2) reverse the redness already present.

Example 8

Rosacea Clinical Study

The 30 subjects with mild to moderate rosacea were treated either with lotion containing 1% w 4-EB (20 subjects) or with a control lotion with the active material removed. The study was randomized and double blinded. During their first visit, patients were evaluated using 4 measurements of disease: 1) erythema, 2) desquamation (peeling), 3) uneven skin tone, and 4) dermatitis. The clinician also provided an "Overall Severity" score which ranged from 1-6 with 6 being the most severe level of overall disease. Patients were photographed to record the severity of the disease. After evaluation patients were sent home with either the test lotion or the control lotion and told to apply it morning and evening for two weeks. They then returned to the clinic for a two-week evaluation and at that time received more product for an additional 2 weeks. At four weeks, both the clinician and the subjects evaluated the severity of their disease. Digital photographs of the treated areas were also taken.

Of the 30 rosacea patients that started the study, 28 completed the four-week period. None of the subjects, including those who dropped out, experienced any irritation or other adverse effect from the product. The bar graph of FIG. 15A summarizes the percentage improvement in "Overall Severity" for the test lotion treated group at 4 weeks. As can be seen, the severity of rosacea decreased in 13/18 subjects (72%). Average improvement among those responding was 68% (49% for all patients). This is a statistically significant result.

The bar graph of FIG. 15B summarizes the percentage improvement in "Overall Severity" for the control lotion treated group at 4 weeks. As can be seen, the severity of rosacea decreased in 6/10 subjects (60%) but increased in 3/10 (30%). Average overall improvement was 15% which is not a significantly significant result.

The test lotion also achieved another important statistical threshold in the rosacea study. The degree of improvement in the test lotion treated group was significantly better than the degree of improvement in the control treated group (p=0.05) using both Wilcoxon and Analysis of Variance statistics. These results are of sufficient quality to meet regulatory standards for drug efficacy and clearly establish the ability of 4-ethoxybenzaldehyde to suppress skin inflammation in humans.

Rosacea is a difficult disease to treat because of the severity of skin inflammation and vasodilation. Considering that a 2% formulation of 4-EB has been shown to be more effective in blocking UV-induced erythema than the 1% formulation used in this clinical study, a higher strength version of the test lotion may provide even greater efficacy in treating rosacea.

The invention claimed is:

1. A method for treating a skin condition of a subject who has a skin condition comprising administering to skin of the subject a composition comprising (1) a pharmaceutically or cosmetically acceptable carrier selected from the group consisting of a lotion, a gel, a cream, a paste, a suspension and an ointment, and (2) an effective skin inflammation-alleviating amount of 4-ethoxybenzaldehyde.

2. The method of claim 1, wherein the skin condition is selected from the group consisting of actinic keratosis, acne, allergic contact dermatitis, atopic eczema, contact dermatitis, eczema, erythema, hand eczema, itch, irritant contact dermatitis, psoriasis, seborrhoric eczema, rosacea, alopecia areata, damage from radiation, and inflammation.

3. The method of claim 1, wherein the pharmaceutically or cosmetically acceptable carrier is a topical carrier and the composition is topically administered to the skin of the subject.

4. The method of claim 1, wherein the pharmaceutically or cosmetically acceptable carrier is a transdermal carrier and the composition is transdermally administered to the skin of the subject.

5. The method of claim 1, wherein the subject is a human.

* * * * *